United States Patent
Vinegar et al.

(10) Patent No.: US 11,099,292 B1
(45) Date of Patent: Aug. 24, 2021

(54) METHOD FOR DETERMINING THE COMPOSITION OF NATURAL GAS LIQUIDS, MEAN PORE-SIZE AND TORTUOSITY IN A SUBSURFACE FORMATION USING NMR

(71) Applicants: Vinegar Technologies LLC, Bellaire, TX (US); William Marsh Rice University, Houston, TX (US)

(72) Inventors: Harold J. Vinegar, Bellaire, TX (US); Philip M. Singer, Richmond, TX (US); George J. Hirasaki, Bellaire, TX (US); Zeliang Chen, Houston, TX (US); Xinglin Wang, Houston, TX (US)

(73) Assignee: Vinegar Technologies LLC, Bellaire, TX (US)

( * ) Notice: Subject to any disclaimer, the term of this patent is extended or adjusted under 35 U.S.C. 154(b) by 0 days.

(21) Appl. No.: 16/842,928

(22) Filed: Apr. 8, 2020

Related U.S. Application Data

(60) Provisional application No. 62/832,276, filed on Apr. 10, 2019.

(51) Int. Cl.
| | | |
|---|---|---|
| G01V 3/32 | (2006.01) | |
| G01R 33/50 | (2006.01) | |
| G01N 33/00 | (2006.01) | |
| G01N 33/24 | (2006.01) | |

(52) U.S. Cl.
CPC .......... *G01V 3/32* (2013.01); *G01N 33/0016* (2013.01); *G01N 33/241* (2013.01); *G01R 33/50* (2013.01)

(58) Field of Classification Search
CPC .... G01V 3/32; G01N 33/0016; G01N 33/241; G01R 33/50

USPC ........ 324/220–221, 300–324, 333, 338, 346, 324/355, 368, 372

See application file for complete search history.

(56) References Cited

U.S. PATENT DOCUMENTS

| | | | | |
|---|---|---|---|---|
| 6,991,045 B2* | 1/2006 | Vinegar | ................... | G01V 3/26 175/45 |
| 7,309,983 B2* | 12/2007 | Freedman | .............. | G01V 11/00 324/303 |
| 7,526,953 B2* | 5/2009 | Goodwin | ................ | E21B 47/10 250/255 |
| 7,940,043 B2* | 5/2011 | Gao | ........................ | G01N 24/08 324/303 |
| 8,061,444 B2* | 11/2011 | Mullins | ................. | E21B 47/022 175/50 |

(Continued)

OTHER PUBLICATIONS

Chen, Z.; Singer, P. M.; Jun, K.; Vargas, F. P.; Hirasaki, G. J.; Jun, K.; Vargas, F. P.; Hirasaki, G. J. Effects of Bitumen Extraction on the 2D NMR Response of Saturated Kerogen Isolates. Petrophysics 2017, 58, 470-484.

(Continued)

*Primary Examiner* — Dixomara Vargas
*Assistant Examiner* — Sean Curtis
(74) *Attorney, Agent, or Firm* — Momentum IP; Marc Van Dyke

(57) ABSTRACT

New methods for determining the volumetric composition and saturation of methane and NGLs (natural gas liquids: ethane, propane, butane, and pentane) in a petroleum reservoir combining NMR (nuclear magnetic resonance) logging and NMR core analysis and for determining the mean pore-size and tortuosity of the light hydrocarbon-filled porosity in a petroleum reservoir using NMR core analysis.

20 Claims, 28 Drawing Sheets

Saturation Apparatus for Laboratory NMR Measurements

(56) References Cited

U.S. PATENT DOCUMENTS

| | | | |
|---|---|---|---|
| 8,714,246 B2* | 5/2014 | Pop | E21B 7/04 166/264 |
| 9,405,036 B2* | 8/2016 | Kadayam Viswanathan | G01V 3/32 |
| 9,552,462 B2* | 1/2017 | Walters | G16C 20/30 |
| 9,645,277 B2* | 5/2017 | Edwards | G01V 3/32 |
| 10,094,949 B2* | 10/2018 | Chen | G01N 24/081 |
| 10,190,413 B2* | 1/2019 | Smith | H01J 49/0468 |
| 10,260,336 B2* | 4/2019 | Smith | G01N 1/4022 |
| 10,488,545 B2* | 11/2019 | Chen | G01N 24/081 |
| 10,494,919 B2* | 12/2019 | Smith | G01N 1/286 |
| 2006/0055403 A1* | 3/2006 | Freedman | G01V 11/00 324/303 |
| 2009/0256562 A1* | 10/2009 | Gao | G01N 33/2835 324/308 |
| 2009/0288881 A1* | 11/2009 | Mullins | E21B 7/04 175/50 |
| 2011/0088895 A1* | 4/2011 | Pop | E21B 7/04 166/254.2 |
| 2012/0296617 A1* | 11/2012 | Zuo | E21B 49/082 703/10 |
| 2013/0113480 A1* | 5/2013 | Kadayam Viswanathan | G01V 3/32 324/303 |
| 2013/0161502 A1* | 6/2013 | Pomerantz | G01N 33/2823 250/255 |
| 2013/0234703 A1* | 9/2013 | Chen | G01N 24/081 324/303 |
| 2014/0225607 A1* | 8/2014 | Edwards | G01V 3/32 324/303 |
| 2014/0238670 A1* | 8/2014 | Pop | E21B 49/087 166/264 |
| 2015/0168588 A1* | 6/2015 | Vinegar | G01V 3/06 702/7 |
| 2015/0184500 A1* | 7/2015 | Vinegar | C10G 45/00 166/303 |
| 2015/0210917 A1* | 7/2015 | Vinegar | E21B 43/24 166/266 |
| 2015/0329785 A1* | 11/2015 | Vinegar | C10G 1/02 507/242 |
| 2016/0091389 A1* | 3/2016 | Zuo | E21B 49/082 73/49.2 |
| 2018/0195383 A1* | 7/2018 | Smith | H01J 49/0422 |
| 2018/0306031 A1* | 10/2018 | Smith | G01N 3/40 |
| 2018/0355717 A1* | 12/2018 | Smith | G01N 3/40 |
| 2019/0017377 A1* | 1/2019 | He | G01N 33/2823 |
| 2019/0025453 A1* | 1/2019 | Chen | G01N 24/081 |
| 2020/0224080 A1* | 7/2020 | Nevison | C09K 8/594 |

OTHER PUBLICATIONS

Fleury, M.; Romero-Sarmiento, M. Characterization of Shales Using T1-T2 NMR Maps. Journal of Petroleum Science and Engineering 2016, 137, 55-62.

Hürlimann, M. D.; Helmer, K. G.; Latour, L. L.; Sotak, C. H. Restricted Diffusion in Sedimentary Rocks. Determination of Surface-Area-to-Volume Ratio and Surface Relaxivity. Journal of Magnetic Resonance, Series A 1994, 111, 169-178.

Hürlimann, M. D.; Freed, D. E.; Zielinski, L. J.; Song, Y. Q.; Leu, G.; Straley, C.; Minh, C. C.; Boyd, A. Hydrocarbon Composition from NMR Diffusion and Relaxation Data. Petrophysics 2009, 50, 116-129.

Kausik, R.; Minh, C. C.; Zielinski, L.; Vissapragada, B.; Akkurt, R.; Song, Y.; Liu, C.; Jones, S.; Blair, E. Characterization of Gas Dynamics in Kerogen Nanopores by NMR. SPE 147198, 2011, 1-16.

Kausik, R.; Fellah, K.; Rylander, E.; Singer, P. M.; Lewis, R. E.; Sinclair, S. M. NMR Relaxometry in Shale and Implications for Logging. Petrophysics 2016, 57, 339-350.

Krynicki, K.; Green, C. D.; Sawyer, D. W. Pressure and Temperature Dependence of Self-Diffusion in Water. Faraday Discussions of the Chemical Society 1978, 66, 199-208.

Latour, L. L.; Mitra, P. P.; Kleinberg, R. L.; Sotak, C. H. Time-Dependent Diffusion Coefficient of Fluids in Porous Media as a Probe of Surface-to-Volume Ratio. Journal of Magnetic Resonance, Series A 1993, 101, 342-346.

Lo, S.-W.; Hirasaki, G. J.; House, W. V.; Kobayashi, R. Mixing Rules and Correlations of NMR Relaxation Time with Viscosity, Diffusivity, and Gas/Oil Ratio of Methane/Hydrocarbon Mixtures. Society of Petroleum Engineers (SPE) Journal 2002, 7, 1-4.

Minh, C. C.; Crary, S.; Singer, P. M.; Valori, A.; Bachman, N.; Hursan, G. G.; Ma, S. M.; Belowi, A.; Kraishan, G. Determination of Wettability from Magnetic Resonance Relaxation and Diffusion Measurements on Fresh-State Cores. SPWLA 56th Annual Logging Symposium 2015.

Mitchell, J.; Gladden, L. F.; Chandrasekera, T. C.; Fordham, E. J. Low-Field Permanent Magnets for Industrial Process and Quality Control. Progress in Nuclear Magnetic Resonance Spectroscopy 2014, 76, 1-60.

Wang, H. J.; Mutina, A.; Kausik, R. High-field Nuclear Magnetic Resonance Observation of Gas Shale Fracturing by Methane Gas. Energy & Fuels 2014, 28, 3638-3644.

Yang, Z.; Hirasaki, G. J.; Appel, M.; Reed, D. A. Viscosity Evaluation for NMR Well Logging of Live Heavy Oils. Petrophysics 2012, 53, 22-37.

Oosting, P. H.; Trappeniers, N. J. Proton Spin-Lattice Relaxation and Self-Diffusion in Methanes. IV. Self-diffusion in methane. Physica 1971, 51, 418-431.

Singer, P. M.; Chen, Z.; Hirasaki, G. J. Fluid Typing and Pore Size in Organic Shale using 2D NMR in Saturated Kerogen. Petrophysics 2016, 57, 604-619.

Singer, P. M.; Chen, Z.; Alemany, L. B.; Hirasaki, G. J.; Zhu, K.; Xie, Z. H. Z. H.; Vo, T. D. NMR Relaxation of Polymer-Alkane Mixes, A Model System for Crude Oils. SPWLA 58th Annual Logging Symposium 2017.

Singer, P. M.; Asthagiri, D.; Chapman, W. G.; Hirasaki, G. J. Molecular Dynamics Simulations of NMR Relaxation and Diffusion of Bulk Hydrocarbons and Water. Journal of Magnetic Resonance 2017, 277, 15-24.

Singer, P. M.; Chen, Z.; Alemany, L. B.; Hirasaki, G. J.; Zhu, K.; Xie, Z. H.; Vo, T. D. Interpretation of NMR Relaxation in Bitumen and Organic Shale Using Polymer-Heptane Mixes. Energy & Fuels 2018, 32, 1534-1549.

Singer, P. M.; Asthagiri, D.; Chapman, W. G.; Hirasaki, G. J. NMR Spin-Rotation Relaxation and Diffusion of Methane. The Journal of Chemical Physics 2018, 148.

Singer, P. M.; Asthagiri, D.; Chen, Z.; Valiya Parambathu, A.; Hirasaki, G. J.; Chapman, W. G. Role of Internal Motions and Molecular Geometry on the NMR Relaxation of Hydrocarbons. Journal of Chemical Physics 2018, 148.

Sigal, R. F. Pore-Size Distributions for Organic-Shale-Reservoir Rocks from Nuclear-Magnetic-Resonance Spectra Combined with Adsorption Measurements. Society of Petroleum Engineers (SPE) Journal 2015, 20, 1-7.

Them, H.; Horch, C.; Stallmach, F.; Li, B.; Mezzatesta, A.; Zhang, H.; Arro, R. Low-field NMR Laboratory Measurements of Hydrocarbons Confined in Organic Nanoporous Media at Various Pressures. Microporous and Mesoporous Materials 2018, 269, 21-25.

Tinni, A.; Sondergeld, C.; Rai, C. New Perspectives on the Effects of Gas Adsorption on Storage and Production of Natural Gas from Shale Formations. 2018, 59, 99-104.

Valori, A.; Van Den Berg, S.; Ali, F.; Abdallah, W. Permeability Estimation from NMR Time Dependent Methane Saturation Monitoring in Shales. Energy & Fuels 2017, 31, 5913-5925.

Venkataramanan, L.; Song, Y.; Hürlimann, M. D. Solving Fredholm Integrals of the First Kind with Tensor Product Structure in 2 and 2.5 Dimensions. IEEE Transaction on Signal Processing 2002, 50 (5), 1017-1026.

* cited by examiner

Saturation Apparatus for Laboratory NMR Measurements

Diagram of MREX logging tool in 8" and 12" boreholes

METHOD FOR DETERMINING THE COMPOSITION OF NATURAL GAS LIQUIDS, MEAN PORE-SIZE AND TORTUOSITY IN A SUBSURFACE FORMATION USING NMR

CROSS-REFERENCE TO RELATED APPLICATIONS

This patent application claims the benefit of U.S. Provisional Patent Application No. 62/832,276 filed on Apr. 10, 2019, which is incorporated herein by reference in its entirety.

FIELD OF THE INVENTION

The present invention relates to petroleum reservoir fluid and petrophysical characterization. In particular, the present invention is useful for quantifying light hydrocarbons in a petroleum reservoir using NMR logging and core analysis as well as determining pore size and tortuosity of the light hydrocarbon-filled porosity using NMR core analysis.

BACKGROUND OF THE INVENTION

Recent advances in horizontal drilling and hydraulic fracturing have enabled methane and natural gas liquids (NGLs) production from tight reservoirs. However, there is an economic difference in value between methane and the NGLs ethane, propane, butane and pentane. Whereas methane is a gas used for heating and electricity, with relatively low value in the US (~$4.50/MCF), propane and butane sell for approximately the same value as oil (~$60/barrel). Ethane is also highly prized because of its use as petrochemical feedstock in manufacturing ethylene. Pentane is a major component of gasoline and very valuable in the US market.

In addition to the economic differences, the methane and NGL composition play a critical role in reservoir engineering. For example, in unconventional tight rock shale, such as the Eagle Ford formation, the most economic regions are the wet gas plays with high NGL saturation, whereas the oil plays may have insufficient production rates, and the dry gas zones produce only a relatively low value product (methane).

Thus, being able to use NMR logging to predict the methane and NGL compositions in the petroleum reservoir can have significant utility to petroleum engineers.

The fast-paced growth in global gas and NGLs production has stimulated research in NMR logging for formation evaluation of tight reservoirs (Hürlimann et al., 2009; Kausik et al., 2011; Wang et al., 2014; Sigal et al., 2015; Fleury et al., 2016; Valori et al., 2017; Tinni et al., 2018; Thern et al., 2018).

NMR measurements on methane-saturated tight rocks are valuable but challenging due to the lower hydrogen index (HI) compared to other liquid-state hydrocarbons. Several recent NMR studies on methane demonstrate the capability of standard low-field NMR (2.3 MHz) bench-top spectrometer and logging tool to capture the signal from methane at achievable pressures. Kausik et al. (2011) investigates the dynamics of methane in kerogen and reports the $T_2$ and diffusivity of methane are greatly reduced in shale, while the HI is increased, compared to the bulk state. Valori et al. (2017) develops a new methodology to estimate permeability of gas-bearing shale rock using NMR-measured methane-saturated $T_2$. Tinni et al. (2018) conducts research to illustrate the effect of methane adsorption on gas production through laboratory NMR measurements.

Diffusivity D measurement by NMR is widely implemented for composition estimation. Hürlimann et al. (2009) reports that D-$T_2$ measurement contains detailed information about the composition of hydrocarbons. It has been demonstrated that methane can be identified by high diffusivity values, even when dissolved in crude oil or kerogen (Hürlimann et al., 2009; Kausik et al., 2011).

Our invention relates to the evaluation of downhole methane and NGLs composition by integrating NMR logging and NMR core analysis. As core containing methane and NGLs is obtained from a downhole formation and brought to the surface, these light hydrocarbons are expelled and evaporate from the core as the pressure is reduced and the core is transported to a core analysis laboratory and stored. Thus, laboratory NMR on as-received cores do not detect the methane and NGLs that are measured with the downhole NMR logging tool. The main problem solved by this invention is how to evaluate the downhole methane and NGL composition and saturations in the NMR log even though they have been released from the core.

The mean pore size and tortuosity of the light hydrocarbon-filled porosity in a petroleum reservoir formation play critical roles in reservoir engineering because they are related to the permeability of the formation. For example, in unconventional tight rock shale, the oil and gas reservoirs must have high enough permeability for economic production rates. The smaller the mean pore size and the more tortuous the flow path, the lower the permeability of the reservoir.

Prior work has used xenon gas diffusion NMR studies at pressures to 6.5 bar for determining pore size and tortuosity in glass bead packs (Mair et al, 2002). Some of the problems with xenon NMR are the need to use high-field superconducting magnets; the need for isotopic enrichment with $^{129}$Xe; problems with the NMR pulse sequence due to diffusion during the gradient pulse; and problems with magnetic susceptibility contrast due to the high magnetic fields.

What is needed is a method for determining the mean pore size and tortuosity of the light hydrocarbon-filled porosity in a petroleum reservoir using a low-field NMR spectrometer that is suitable for core analysis laboratories.

SUMMARY OF THE INVENTION

In this invention, the core analysis consists of pressure saturation of the as-received reservoir core-plugs in a NMR overburden cell, followed by NMR $T_2$ distributions and D-$T_2$ measurements at reservoir conditions. The saturating fluids in the core-plugs include water and light hydrocarbons, including methane, ethane, propane, n-butane, n-pentane and n-decane.

The laboratory-measured $T_2$ distributions of the hydrocarbons in saturated cores are converted to $T_{2app}$ ($T_2$ apparent) distributions by simulating the effects of diffusion in the magnetic-field gradient of the NMR logging tool. The core data indicate a large contrast in $T_{2app}$ distributions between the different hydrocarbons due to different surface relaxivities and diffusivities. This contrast is used to estimate the downhole hydrocarbon composition by minimizing the least-square error in the $T_{2app}$ distributions between core and log data.

Each of the laboratory-measured $T_2$ distributions of the methane and NGLs are transformed to downhole-measured $T_{2app}$ distributions by simulating the magnetic-field gradient effect from the logging tools. The $T_{2app}$ distributions of methane and NGLs are used as a basis set for numerically mixing the hydrocarbons to find the volume fractions that result in the best (least-squares) match with the log.

Once the volumetric composition of C1, C2, C3, C4, and C5 are known, one can compute the ratios of the various components, such as C2/C1, C3/C1, C2/C3, (C2+C3+C4+C5)/C1, etc. These ratios are important in geochemical exploration. For example, they relate to source rock maturity, leaking seals, etc.

The invention thus has the following steps:
 a. Obtaining core in selected zones from the reservoir formation.
 b. Obtaining density and NMR log of T2app (T2 apparent) distribution opposite the cored zones using a gradient-based NMR logging tool.
 c. Estimating pressure and temperature of the methane and NGLs at depth in the formation to estimate fluid density and Hydrogen Index.
 d. Re-saturating core in the laboratory with methane and pure NGLs (ethane, propane, butane and pentane) at estimated formation pressure and temperature.
 e. Measuring NMR on the core in the laboratory including T2 distribution and D-T2 with C1-C5 (methane-pentane) in the core, at ~2 MHz (i.e. the same magnetic field as the NMR logging tool).
 f. Using the known magnetic field gradients of the NMR logging tool to convert T2 into T2app for the core data, thereby determining T2app distribution with C1-C5 in the core.
 g. Using the known (1) pressure and temperature, and (2) T2app-distributions for C1-C5 saturated cores, computing the numerical mixture of methane and NGLs core data that best matches the T2app-distribution in the NMR logs, thereby determining the C1-C5 volumetric composition of the reservoir.

This invention is also a method for determining the mean pore-size and tortuosity of the light hydrocarbon-filled porosity using NMR restricted diffusion measurements. The mean pore-size and tortuosity of the light-hydrocarbon-filled porosity are closely related to the hydrocarbon permeability, which determines the hydrocarbon producibility of a formation. These petrophysical properties play critical roles in reservoir engineering.

The invention also consists of the following steps:
 a) Obtaining core in selected zones from the reservoir formation.
 b) Measuring NMR on the core in the laboratory including normalized diffusion coefficient D/Do as a function of diffusion time using one or more hydrogen-bearing fluids selected from the list ($H_2$, HD, $CH_4$, $C_2H_6$, $C_3H_8$, $C_4H_{10}$, $C_5H_{12}$) saturating the core.
 c) Varying the pressure and/or temperature of the one or more hydrogen-bearing fluids to vary the diffusion length in the NMR measurement, and
 d) Computing the mean pore-size and tortuosity of the light hydrocarbon-filled porosity of the reservoir formation from D/Do versus diffusion length of the hydrogen-bearing fluid using a numerical model for restricted diffusion in a porous medium.

Some embodiments relate to a method of using NMR to determine methane plus NGLs composition in a reservoir formation by:
 a. Obtaining core in selected zones from the reservoir formation.
 b. Obtaining density and NMR log of $T_{2app}$ ($T_2$ apparent) distribution opposite the cored zones using a gradient-based NMR logging tool.
 c. Estimating pressure and temperature of the methane and NGLs at depth in the cored zones to estimate fluid density and Hydrogen Index.
 d. Re-saturating core in the laboratory with methane and pure NGLs (ethane, propane, butane and pentane) at estimated formation pressure and temperature.
 e. Measuring NMR on the core in the laboratory including $T_2$ distribution and D-$T_2$ with C1-C5 (methane-pentane) in the core, at ~2 MHz (i.e. the same magnetic field as the NMR logging tool).
 f. Using the known magnetic field gradients of the NMR logging tool to convert $T_2$ into $T_{2app}$ for the core data, thereby estimating the $T_{2app}$ distribution with C1-C5 in the core.
 g. Using the known (1) pressure and temperature, and (2) $T_{2app}$—distributions for C1-C5 saturated cores, computing the numerical mixture of methane and NGLs core data that best matches the $T_{2app}$-distribution in the logs ($T_{2app}$>36 ms, or other cutoff), thereby determining the C1-C5 composition in the reservoir formation.

Some embodiments relate to a method of using NMR to determine the mean pore-size and tortuosity of the light hydrocarbon-filled porosity in a reservoir formation by:
 a) Obtaining core in selected zones from the reservoir formation.
 b) Measuring NMR on the core in the laboratory including normalized diffusion coefficient $D/D_0$ as a function of diffusion evolution-time using one or more hydrogen-bearing fluids selected from the list ($H_2$, HD, $CH_4$, $C_2H_6$, $C_3H_8$, $C_4H_{10}$, $C_5H_{12}$) saturating the core.
 c) Varying the pressure and/or temperature of the one or more hydrogen-bearing fluids to vary the diffusion length in the NMR measurement, and
 d) Computing the mean pore-size and tortuosity of the light hydrocarbon-filled porosity of the reservoir formation from $D/D_0$ versus diffusion length of the hydrogen-bearing fluid using a numerical model for restricted diffusion in a porous medium.

Some embodiments relate to a method of measuring at least one of: (i) respective downhole concentrations in a subsurface formation of one or more members of the C1-C5 alkane group consisting of methane, ethane, propane, butane and pentane; and (ii) a mathematical relation between respective downhole concentrations of multiple members of the C1-C5 alkane group, the method comprising:
 a. obtaining sample(s) of core from a target depth in a subsurface formation;
 b. obtaining downhole NMR log data of the subsurface formation at the target depth;
 c. when a given one of the core sample(s) is saturated with a first pressurized saturation fluid comprising (e.g. dominated by) a first member of the C1-C5 alkane group, obtaining first laboratory NMR data of the saturated core-sample(s); and
 d. when the same given one or a different one of the core sample(s) is saturated with a second pressurized saturation fluid that is different from the first pressurized saturation fluid, the second saturation fluid comprising (e.g. dominated by) a second member of the C1-C5 alkane group that is different from the first member, obtaining second laboratory NMR data of the saturated core-sample(s), wherein the first and second laboratory NMR collectively form a laboratory NMR data set, and wherein the method further comprises:

e. computing from the lab-NMR data set and the downhole NMR log data at least one downhole parameter selected from the group consisting of: (i) respective downhole concentrations of one or more members of the C1-C5 alkane group consisting of methane, ethane, propane, butane and pentane; and (ii) a mathematical relation between respective downhole concentrations of multiple members of the C1-C5 alkane group.

In some embodiments,
i. the method further comprises: when the same given one or a different one of the core sample(s) is saturated with a third pressurized saturation fluid comprising (e.g. dominated by) a third member of the C1-C5 alkane group that is different from the first and second members, obtaining third laboratory NMR data of the saturated core-sample(s); and
ii. the third pressurized saturation fluid is different from both of the first and second pressurized saturation fluids; and
iii. the first, second and third laboratory NMR data collectively form the laboratory NMR data set.

In some embodiments,
i. the method further comprises: when the same given one or a different one of the core sample(s) is saturated with a fourth pressurized saturation fluid comprising (e.g. dominated by) a fourth member of the C1-C5 alkane group that is different from the first, second and third members, obtaining fourth laboratory NMR data of the saturated core-sample(s); and
ii. the $4^{th}$ pressurized saturation fluid is different from all of the first, second, and $3^{rd}$ pressurized saturation fluids; and
iii. the first, second, third and fourth laboratory NMR data collectively form the laboratory NMR data set.

In some embodiments,
i. the method further comprises: when the same given one or a different one of the core sample(s) is saturated with a fifth pressurized saturation fluid comprising (e.g. dominated by) a fifth member of the C1-C5 alkane group that is different from the first, second, third and fourth members, obtaining fifth laboratory NMR data of the saturated core-sample(s); and
ii. the fifth pressurized saturation fluid is different from all of the first, second, $3^{rd}$ and $4^{th}$ pressurized saturation fluids; and
iii. the first, second, third, fourth and fifth laboratory NMR data collectively form the laboratory NMR data set.

In some embodiments, the laboratory NMR data set comprises data obtained when core(s) sample(s) is saturated with a pressurized saturation fluid dominated by methane.

In some embodiments, the laboratory NMR data set comprises data obtained when core(s) sample(s) is saturated with a pressurized saturation fluid dominated by ethane.

In some embodiments, the laboratory NMR data set comprises data obtained when core(s) sample(s) is saturated with a pressurized saturation fluid dominated by propane.

In some embodiments, the laboratory NMR data set comprises data obtained when core(s) sample(s) is saturated with a pressurized saturation fluid dominated by butane.

In some embodiments, the laboratory NMR data set comprises data obtained when core(s) sample(s) is saturated with a pressurized saturation fluid dominated by pentane.

In some embodiments, the downhole pressure and temperature are estimated for the subsurface formation at the target depth, and wherein the $1^{st}$ and/or $2^{nd}$ and/or $3^{rd}$ and/or $4^{th}$ and/or $5^{th}$ laboratory NMR data is obtained when the core sample(s) are saturated with the first and/or second and/or third and/or fourth and/or fifth pressurized fluid at the estimated pressure and temperature.

In some embodiments, the laboratory NMR data and/or downhole NMR log data comprises one or more of (i.e. any combination of): T2 distribution data, T2apparent distribution data, T1 distribution data, T1/T2 data, T1/T2apparent, D (diffusion) vs. T2 data, D (diffusion) vs T2apparent data.

In some embodiments, the computing of the at least one downhole parameter comprises optimizing a fit of:
i. a mathematical combination of the $1^{st}$ and/or $2^{nd}$ and/or $3^{rd}$ and/or $4^{th}$ and/or $5^{th}$ laboratory NMR data; to
ii. downhole NMR data.

In some embodiments, the computed downhole concentration and/or computed molar fraction of the $1^{st}$ and/or $2^{nd}$ and/or $3^{rd}$ and/or $4^{th}$ and/or $5^{th}$ member of the C1-C5 alkane group corresponds to a weighting coefficient for the $1^{st}$ and/or $2^{nd}$ and/or $3^{rd}$ and/or $4^{th}$ and/or $5^{th}$ laboratory NMR data.

In some embodiments, the method is performed to compute at least one of the following: (i) a ratio between a downhole methane concentration and a downhole ethane concentration; (ii) a ratio between a downhole methane concentration and a downhole propane concentration; (iii) a ratio between a downhole methane concentration and a downhole butane concentration; (iv) a ratio between a downhole methane concentration and a downhole pentane concentration; and/or (v) any ratio involving any of C1-C5 alkane group.

In some embodiments, the method is performed to compute at least one of the following: (i) a multi-alkane sum of downhole concentrations of ethane and/or propane and/or butane and/or pentane; and (ii) a ratio the multi-alkane sum and a downhole methane concentration.

In some embodiments, the method is performed for a plurality of target depths to characterize the subsurface reservoir at multiple target depths.

In some embodiments, the computing comprises converting T2 data into $T2_{apparent}$ data or vice versa using at least one of: (i) an estimated diffusion coefficient (e.g. restricted diffusion coefficient) for one or more members of the C1-C5 alkane group; and/or (ii) an estimated mean pore-size of the core sample(s).

In some embodiments, the restricted coefficient is computed by interpolating the following method:

A method using NMR to determine the mean pore-size and tortuosity of the light hydrocarbon-filled porosity in a reservoir formation by:
a) Obtaining core in selected zones from the reservoir formation.
b) Measuring NMR on the core in the laboratory including normalized diffusion coefficient D/Do as a function of diffusion time using one or more hydrogen-bearing fluids selected from the list ($H_2$, HD, $CH_4$, $C_2H_6$, $C_3H_8$, $C_4H_{10}$, $C_5H_{12}$) saturating the core.
c) Varying the pressure and/or temperature of the one or more hydrogen-bearing fluids to vary the diffusion length in the NMR measurement, and
d) Computing the mean pore-size and tortuosity of the light hydrocarbon-filled porosity of the reservoir formation from D/Do versus diffusion length of the hydrogen-bearing fluid using a numerical model for restricted diffusion in a porous medium.

In some embodiments, for two candidate saturation fluids (e.g. the $1^{st}$ and $2^{nd}$ saturation fluid, $1^{st}$ and $3^{rd}$ saturation fluid, $1^{st}$ and $4^{th}$ saturation fluid, $1^{st}$ and $5^{th}$ saturation fluid, $2^{nd}$ and $3^{rd}$ saturation fluid, $2^{nd}$ and $4^{th}$ saturation fluid, $2^{nd}$ and $5^{th}$ saturation fluid, $3^{rd}$ and $4^{th}$ saturation fluid, $3^{rd}$ and $5^{th}$ saturation fluid and/or $4^{th}$ and $5^{th}$ saturation fluid—this condition may apply for ANY two different saturation fluids that can be designated as 'candidates') selected from the group consisting of the $1^{st}$, $2^{nd}$, $3^{rd}$, $4^{th}$, and $5^{th}$ saturation fluids:
  i. a methane-richer saturation fluid is the saturation fluid of the two candidates having the higher methane concentration and a methane-poorer saturation fluid is the saturation fluid of the two candidates having the lower methane concentration; and
  ii. a ratio between a methane concentration in the methane-richer saturation fluid and a methane concentration in the methane-poorer saturation fluid is at least 1.1 or at least 1.25 or at least 1.5 or at least 2 or at least 5 or at least 7.5 or at least 10.

In some embodiments, a mole fraction of the methane-richer saturation fluid is at least 0.1 or at least 0.2 or at least 0.3 or at least 0.4 or at least 0.5.

In some embodiments, a mole fraction of the methane-poorer saturation fluid is zero or at most 0.1.

In some embodiments, for two candidate saturation fluids (e.g. the $1^{st}$ and $2^{nd}$ saturation fluid, $1^{st}$ and $3^{rd}$ saturation fluid, $1^{st}$ and $4^{th}$ saturation fluid, $1^{st}$ and $5^{th}$ saturation fluid, $2^{nd}$ and $3^{rd}$ saturation fluid, $2^{nd}$ and $4^{th}$ saturation fluid, $2^{nd}$ and $5^{th}$ saturation fluid, $3^{rd}$ and $4^{th}$ saturation fluid, $3^{rd}$ and $5^{th}$ saturation fluid and/or $4^{th}$ and $5^{th}$ saturation fluid—this condition may apply for ANY two different saturation fluids that can be designated as 'candidates') selected from the group consisting of the $1^{st}$, $2^{nd}$, $3^{rd}$, $4^{th}$, and $5^{th}$ saturation fluids:
  i. an ethane-richer saturation fluid is the saturation fluid of the two candidates having the higher ethane concentration and a ethane-poorer saturation fluid is the saturation fluid of the two candidates having the lower ethane concentration; and
  ii. a ratio between an ethane concentration in the ethane-richer saturation fluid and an ethane concentration in the ethane-poorer saturation fluid is at least 1.1 or at least 1.25 or at least 1.5 or at least 2 or at least 5 or at least 7.5 or at least 10.

In some embodiments, a mole fraction of the ethane-richer saturation fluid is at least 0.1 or at least 0.2 or at least 0.3 or at least 0.4 or at least 0.5.

In some embodiments, a mole fraction of the ethane-poorer saturation fluid is zero or at most 0.1.

In some embodiments, for two candidate saturation fluids (e.g. the $1^{st}$ and $2^{nd}$ saturation fluid, $1^{st}$ and $3^{rd}$ saturation fluid, $1^{st}$ and $4^{th}$ saturation fluid, $1^{st}$ and $5^{th}$ saturation fluid, $2^{nd}$ and $3^{rd}$ saturation fluid, $2^{nd}$ and 4th saturation fluid, $2^{nd}$ and $5^{th}$ saturation fluid, $3^{rd}$ and $4_{th}$ saturation fluid, $3^{rd}$ and $5^{th}$ saturation fluid and/or $4^{th}$ and $5^{th}$ saturation fluid—this condition may apply for ANY two different saturation fluids that can be designated as 'candidates') selected from the group consisting of the $1^{st}$, $2^{nd}$, $3^{rd}$, $4^{th}$, and $5^{th}$ saturation fluids:
  i. a propane-richer saturation fluid is the saturation fluid of the two candidates having the higher propane concentration and a propane-poorer saturation fluid is the saturation fluid of the two candidates having the lower propane concentration; and
  ii. a ratio between a propane concentration in the propane-richer saturation fluid and a propane concentration in the propane-poorer saturation fluid is at least 1.1 or at least 1.25 or at least 1.5 or at least 2 or at least 5 or at least 7.5 or at least 10.

In some embodiments, a mole fraction of the propane-richer saturation fluid is at least 0.1 or at least 0.2 or at least 0.3 or at least 0.4 or at least 0.5.

In some embodiments, a mole fraction of the propane-poorer saturation fluid is zero or at most 0.1.

In some embodiments, for two candidate saturation fluids (e.g. the $1^{st}$ and $2^{nd}$ saturation fluid, $1^{st}$ and $3^{rd}$ saturation fluid, $1^{st}$ and $4_th$ saturation fluid, $1^{st}$ and $5^{th}$ saturation fluid, $2^{nd}$ and $3^{rd}$ saturation fluid, $2^{nd}$ and $4^{th}$ saturation fluid, $2^{nd}$ and $5^{th}$ saturation fluid, $3^{rd}$ and $4^{th}$ saturation fluid, $3^{rd}$ and $5^{th}$ saturation fluid and/or $4^{th}$ and $5^{th}$ saturation fluid—this condition may apply for ANY two different saturation fluids that can be designated as 'candidates') selected from the group consisting of the $1^{st}$, $2^{nd}$, $3^{rd}$, $4^{th}$, and $5^{th}$ saturation fluids:
  i. a butane-richer saturation fluid is the saturation fluid of the two candidates having the higher butane concentration and a butane-poorer saturation fluid is the saturation fluid of the two candidates having the lower butane concentration; and
  ii. a ratio between a butane concentration in the butane-richer saturation fluid and a butane concentration in the butane-poorer saturation fluid is at least 1.1 or at least 1.25 or at least 1.5 or at least 2 or at least 5 or at least 7.5 or at least 10.

In some embodiments, a mole fraction of the butane-richer saturation fluid is at least 0.1 or at least 0.2 or at least 0.3 or at least 0.4 or at least 0.5.

In some embodiments, a mole fraction of the butane-poorer saturation fluid is zero or at most 0.1.

In some embodiments, for two candidate saturation fluids (e.g. the $1^{st}$ and $2^{nd}$ saturation fluid, $1^{st}$ and $3^{rd}$ saturation fluid, $1^{st}$ and $4^{th}$ saturation fluid, $1^{st}$ and $5^{th}$ saturation fluid, $2^{nd}$ and $3^{rd}$ saturation fluid, $2^{nd}$ and 4th saturation fluid, $2^{nd}$ and $5^{th}$ saturation fluid, $3^{rd}$ and $4^{th}$ saturation fluid, $3^{rd}$ and $5^{th}$ saturation fluid and/or $4^{th}$ and $5^{th}$ saturation fluid—this condition may apply for ANY two different saturation fluids that can be designated as 'candidates') selected from the group consisting of the $1^{st}$, $2^{nd}$, $3^{rd}$, $4^{th}$, and $5^{th}$ saturation fluids:
  i. a pentane-richer saturation fluid is the saturation fluid of the two candidates having the higher pentane concentration and a pentane-poorer saturation fluid is the saturation fluid of the two candidates having the lower pentane concentration; and
  ii. a ratio between a pentane concentration in the pentane-richer saturation fluid and a pentane concentration in the pentane-poorer saturation fluid is at least 1.1 or at least 1.25 or at least 1.5 or at least 2 or at least 5 or at least 7.5 or at least 10.

In some embodiments, a mole fraction of the pentane-richer saturation fluid is at least 0.1 or at least 0.2 or at least 0.3 or at least 0.4 or at least 0.5.

In some embodiments, a mole fraction of the pentane-poorer saturation fluid is zero or at most 0.1.

In some embodiments, the first pressurized saturation fluid is dominated by the first member of the C1-C5 alkane group.

In some embodiments, the second pressurized saturation fluid is dominated by the second member of the C1-C5 alkane group.

In some embodiments, the third pressurized saturation fluid is dominated by the third member of the C1-C5 alkane group.

In some embodiments, the fourth pressurized saturation fluid is dominated by the fourth member of the C1-C5 alkane group.

In some embodiments, the fifth pressurized saturation fluid is dominated by the fifth member of the C1-C5 alkane group.

In some embodiments, when a saturation fluid is 'dominated by' by a given member of the C1-C5 alkane group, a mole fraction of the member of the C1-C5 alkane group is at least 0.501 or at least 0.505 or at least 0.51 or least 0.53 or at least 0.55 or at least 0.6 or at least 0.65 or at least 0.7 or at least 0.8 or at least 0.9 or at least 0.95 or at least 0.975 or at least 0.99 or at exactly 1.

In some embodiments, the NMR log is from a gradient-based NMR tool.

DETAILED DESCRIPTION OF THE INVENTION

NMR Measurements

Figure 1:
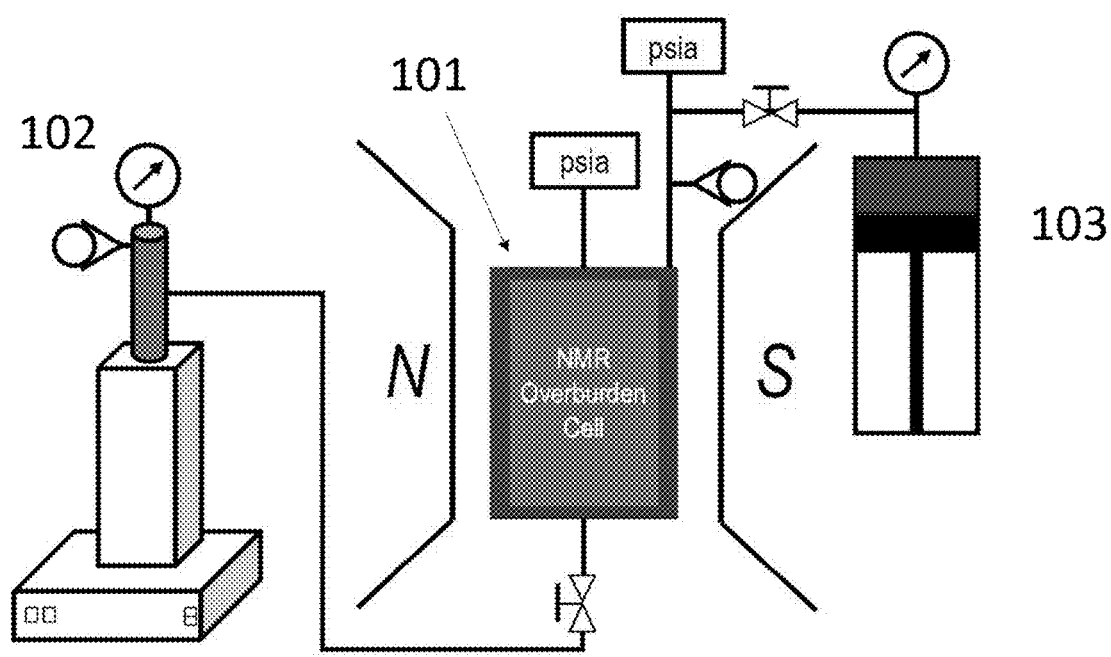
FIG. 1 show a schematic of the NMR spectrometer with laboratory apparatus for fluid saturation used in this invention

An Oxford Instruments (Oxfordshire, UK) GeoSpec2 rock-core analyzer with a resonance frequency of $\omega/2\pi=2.3$ MHz for $^1$H (which is similar to downhole NMR logging tools) is used to acquire the NMR data. The GeoSpec2 is equipped with magnetic field gradients for diffusion measurements. The measurements are conducted in an Oxford Instruments P5 overburden core holder in either laboratory or reservoir conditions (elevated pressure and temperature), which are discussed in the following subsection. The 2-D $T_1$-$T_2$ data are acquired using 32 log-spaced points on an inversion-recovery curve ranging from 0.2 ms to 20,000 ms (typically). Each point on the inversion-recovery curve is followed by a series of CPMG echoes with an echo spacing of $T_E$=0.2 ms. The 2-D D-$T_2$ data are acquired using a unipolar stimulated-echo sequence (Mitchell et al., 2014) with 32 pulsed-field trapezoidal gradient steps ranging from zero to a maximum strength of $g_y$=43 G/cm, a gradient encoding time of $\delta$=9 ms, a diffusion evolution time of $\Delta$=14.7 ms, and a dead time of $T_d$=25 ms. The 2-D correlation maps are processed using the fast inverse Laplace transform (analogous to Venkataramanan et al., 2002) with 120 log-spaced bins for $T_2$ and D. The units of the y-axis on the relaxation time distributions are in "pu/div", which means porosity units per x-axis bin-size. In the case of $T_2$ distribution, the bin size is "div=$\Delta \log_{10}T_2$=($\log_{10}T_{2,i+1}$-$\log_{10}T_{2,i}$)", which is independent of index "i" because of the log-spaced bin selection. This unit of the y-axis is also known as bin porosity.

Core Samples and Fluid Saturations

As an example of how to practice this invention, core samples were obtained from a reservoir of organic-rich bituminous chalks which was then logged by NMR. These organic-rich chalks are tight rocks with a permeability of ~0.01 mD. The TOC (total organic carbon) of the organic-rich chalks is ~10 wt % (or ~20 vol %) and the kerogenous matter is early-stage mature Type II-S kerogen.

Petrophysically, the cores consist of water-wet micritic calcite and intergranular macropores containing kerogen, bitumen, light hydrocarbons, and small quantities of connate water.

The well was drilled with water-based mud. All downhole operations in the reservoir zone were underbalanced to prevent invasion and flushing. At the wellsite, the core was sealed in plastic wrap and aluminum foil and dip coated in low melting paraffin to prevent further evaporation. The core plugs used in this NMR study were drilled from the core with air mist to prevent adding water to the pore space.

The core plugs are 25 mm in diameter and 48 mm in length, which are compatible with the Oxford Instrument NMR overburden core holder. A series of "twin" cores (No. 1 to No. 6) originating from the same depth of the formation are selected for laboratory core analysis. The pore space of the "as-received" core samples consists of bitumen, connate water, and air, as detected by the laboratory NMR core-analyzer (shown in the following section). The cores are then saturated with either water, methane, ethane, propane, n-butane, n-pentane or n-decane for in-situ NMR measurements. Note that n-butane, n-pentane and n-decane are hereafter shortened to butane, pentane, and decane, respectively.

The apparatus diagram for in-situ saturation is shown in FIG. 1. The core samples are placed within the NMR overburden core holder 101 for pressure saturation. A syringe pump 102 is used to inject fluids while a hydraulic hand pump 103 is used to maintain the confining pressure. All pressure saturations are conducted by injecting fluids at constant inlet-pressure with the outlet which is closed and connected to a pressure transducer.

In a preferred mode of practicing this invention, the laboratory NMR measurements are made at the same temperature and pressure as found in the reservoir.

In another mode of practicing this invention, all the NMR measurements are made at laboratory temperature and pressure conditions and the results are then corrected to reservoir conditions. In the following we show how this is done. All the laboratory NMR measurements presented here are performed at a temperature of 30° C. The targeted pore pressure (1,200 psia) is adjusted such that the density of ethane at laboratory conditions would be the same as that at reservoir temperature and pressure (68° C. and 2,755 psia). The pressurization to the targeted pore pressure takes two steps. The cores are initially pressurized from 14.7 psia (ambient pressure) to 500 psia, and then from 500 psia to 1,200 psia. The step-wise pressurization is meant to limit the pressure gradient and effective stress (a.k.a. net pressure, namely the net stress between overburden stress and pore pressure) to avoid irreversible change in the cores. The effective stress is kept constant at 1,000 psi during the NMR measurements.

The details of saturations and measurements are tabulated in Table 1.

TABLE 1

List of core number, saturating fluid, temperature, pore pressure, and confining pressure for NMR measurements on "Twin" cores.

| Core | Fluid | Label | T (° C.) | $P_{pore}$ (psia) | $P_{confining}$ (psia) |
|---|---|---|---|---|---|
| 1 | Propane | C3 | 30 | 1,200 | 2,200 |
|   | $D_2O$ | D2O | 30 | 1,200 | 2,200 |
|   | Methane ($D_2O$) | C1(D2O) | 30 | 1,200 | 2,200 |
| 2 | Methane | C1 | 30 | 1,200 | 2,200 |
|   | Ethane | C2 | 30 | 1,200 | 2,200 |
| 3 | $H_2O$ | H2O | 30 | 1,200 | 2,200 |
| 4 | Pentane | C5 | 30 | 1,200 | 2,200 |
| 5 | Decane | C10 | 30 | 1,200 | 2,200 |
| 6 | Butane | C4 | 30 | 1,200 | 2,200 |

These series of "twin" cores are used in parallel for different saturating fluids because the saturation slightly alters the cores. More specifically, a small amount of connate water may be mobilized and expelled during pressurization and depressurization of light hydrocarbons. Thus, although this invention could be practiced with a single core being saturated and desaturated with hydrocarbons shown in Table 1, it is preferable to use multiple twin samples, if they are available, and use a single hydrocarbon fluid per core plug.

The NMR results on the as-received cores reveal similar NMR responses (shown in the next section for $T_2$). Therefore, no distinction is made between these as-received "twin" cores. The order of saturation listed in Table 1 for core No. 1 and No. 2 follows the order of actual experiments. After each fluid saturation on core No. 1 and No. 2, the cores are depressurized and taken out of the overburden cell to remove excess fluid for the next step. The deuterated core No. 1 (denoted as "D2O") is prepared by immersing the core into fresh D20 brine twice. Each deuteration step lasts for one week at ambient conditions. It should be noted that the "C1 (D2O)" is done by injecting methane into core No. 1, which has been deuterated after propane saturation. The purpose of "C1 (D2O)" is to study the NMR responses of pure methane, without the interference from connate water so that the $T_2$ and diffusivity of the methane can be readily observed.

Bulk Properties of Saturating Fluids

The bulk properties of water and hydrocarbons at both laboratory conditions (30° C., 1,200 psia) and downhole conditions (68° C., 2,755 psia) are acquired and summarized in Table 2. The density and viscosity of fluids are inferred from NIST REFPROP database with temperature and pressure as the inputs. The hydrogen indexes (HI) of fluids other than water are calculated by comparing the proton densities with that of water at the same temperature and pressure. Note that only methane shows significant differences in density and HI under different conditions. Also note that methane under both conditions is a supercritical fluid instead of a gas.

TABLE 2

Bulk properties of fluids on both laboratory and reservoir conditions

| | 30° C., 1,200 psia (laboratory) | | | | 68° C., 2,755 psia (reservoir) | | | |
|---|---|---|---|---|---|---|---|---|
| Fluid | Density (g/cm$^3$) | HI | Viscosity (cP) | Diffusivity (μm$^2$/ms) | Density (g/cm$^3$) | HI | Viscosity (cP) | Diffusivity (μm$^2$/ms) |
| Water (H2O) | 1.00 | 1.00 | 0.797 | 2.3 | 0.99 | 1.00 | 0.420 | 5.6 |
| Methane (C1) | 0.06 | 0.13 | 0.013 | 250.0 | 0.12 | 0.27 | 0.018 | 125.0 |
| Ethane (C2) | 0.36 | 0.65 | 0.047 | 30.1 | 0.35 | 0.64 | 0.046 | 34.5 |
| Propane (C3) | 0.50 | 0.83 | 0.106 | 13.4 | 0.48 | 0.80 | 0.092 | 17.4 |
| Butane (C4) | 0.58 | 0.90 | 0.168 | 8.5 | 0.56 | 0.88 | 0.141 | 11.3 |
| Pentane (C5) | 0.63 | 0.94 | 0.232 | 6.1 | 0.61 | 0.92 | 0.200 | 8.0 |
| Decane (C10) | 0.73 | 1.02 | 0.869 | 1.6 | 0.71 | 1.00 | 0.616 | 2.6 |

The diffusivity of water measured at 25° C. and ambient pressure is used for the laboratory conditions. For the reservoir conditions, Krynicki et al., 1978 measures the diffusivity of water at 70.05° C. and at around 1470 and 4410 psia respectively, which are similar to the reservoir conditions in this work. These two measurements at different pressures both yield diffusivities around 5.6 µm²/ms which is adopted here as the bulk diffusivity of water at reservoir conditions.

The diffusivity of ethane, propane, butane, pentane and decane are estimated by substituting the temperature and viscosity into Equation 1, which is an empirical correlation proposed by Lo et al., 2002:

$$D_0 = 4.69 \times 10^{-3} \frac{T}{\mu}, \quad (1)$$

where $D_0$ is bulk diffusivity with a unit of µm²/ms, T is temperature with a unit of K and µ is viscosity with a unit of cP.

Figure 2:
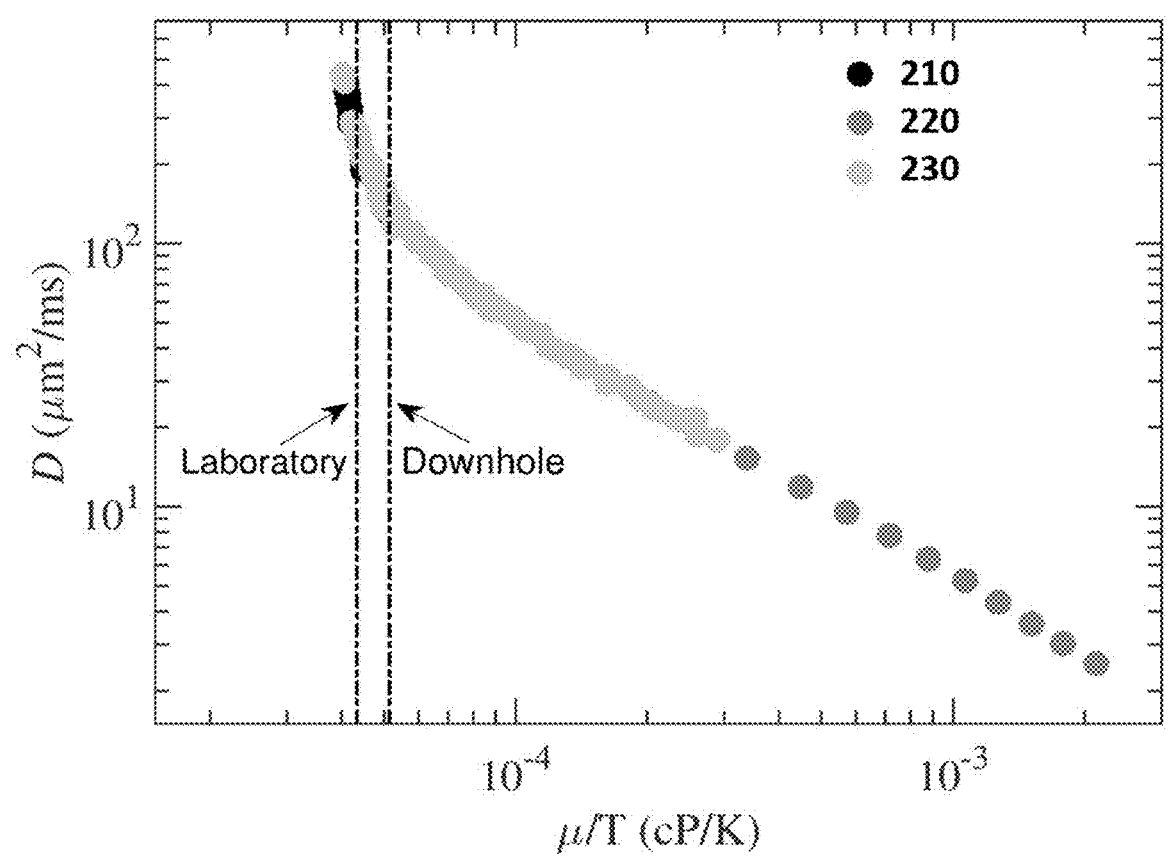
FIG. 2 shows bulk diffusivity D vs. viscosity/temperature $\mu/T$ of methane

The diffusivity of methane is obtained in a different way. It is inferred from the experimental data published by Oosting et al., 1971, who measured the bulk diffusivity of methane as a function of bulk density and temperature. The original data (Oosting et al., 1971) is re-organized and plotted in FIG. 2. The measured bulk diffusivities in different phases are clustered and plotted against the predicted viscosity/temperature (µ/T). The predicted µ/T is inferred from REFPROP based on the bulk density and temperature. It is obvious that the bulk diffusivity of the vaporous 210 and some of the supercritical 230 methane does not follow the Stokes-Einstein equation which predicts that D vs. µ/T is a straight line on a log-log plot like Equation 1 (liquid phase 220). Therefore, the µ/T of methane on both laboratory and reservoir conditions are used to estimate the bulk diffusivity (shown as the two vertical dashed lines in FIG. 2). The µ/T of methane at laboratory conditions suggests a bulk diffusivity ~250 µm²/ms, while methane at downhole conditions yields a bulk diffusivity ~125 µm²/ms. The mismatch in the methane diffusivity between the laboratory and reservoir conditions is a compromise of a better match in the ethane density.

The estimated diffusivities of bulk fluids at laboratory and reservoir conditions are used later to simulate downhole logs and to interpret the restricted diffusion.

Composition Estimation by $T_2$

This section presents $T_2$ laboratory measurements on as-received and saturated cores. This section also shows how the laboratory $T_2$ is used to calibrate the log to estimate the light-hydrocarbon composition.

$T_2$ Distributions of as-Received Cores

Figure 3:
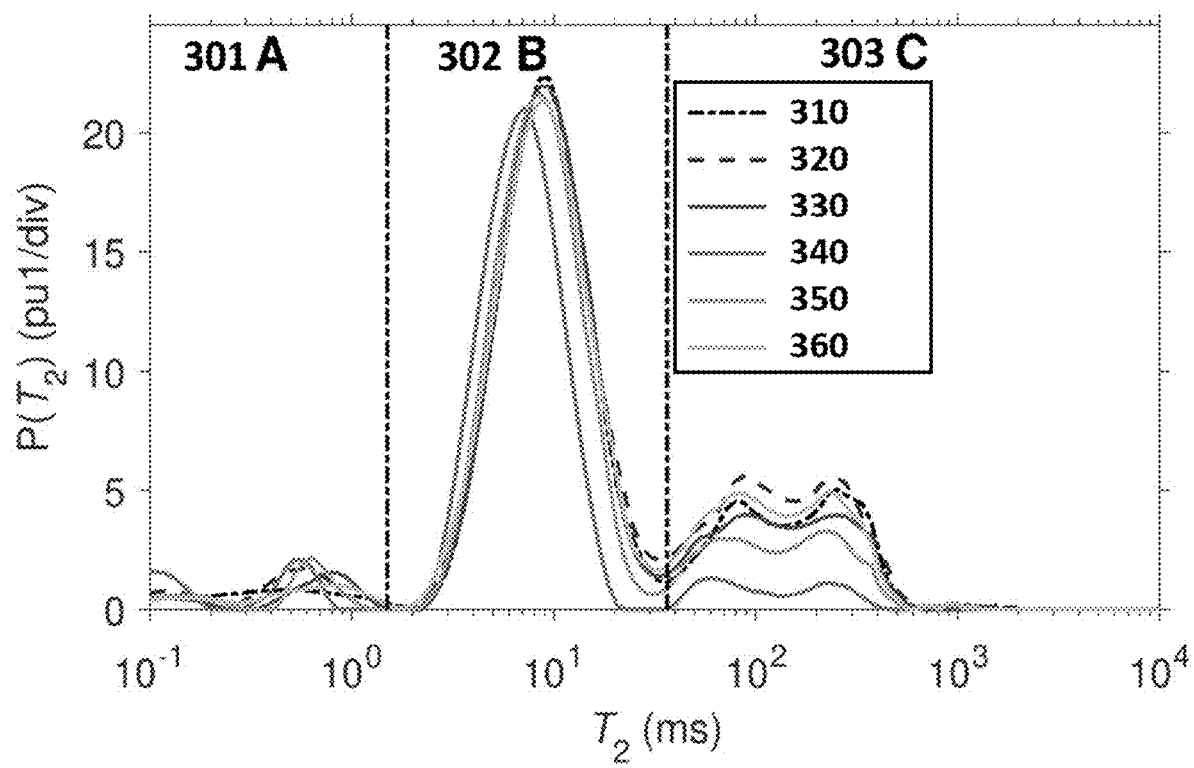
FIG. 3 shows NMR $T_2$ distributions of the as-received cores from the same depth.

FIG. 3 shows the $T_2$ distributions of six as-received cores from the same depth. The $T_2$ distributions can be divided into three regions by the vertical dashed lines, and are identified as: 301 (A) bitumen and/or dissolved light hydrocarbon region (leftmost), which may contain light hydrocarbons dissolved in both bitumen and kerogen; 302 (B) connate water region (middle), and; 303 (C) light hydrocarbon region with small amount of connate water, where most of the connate signal can be eliminated by deuteration (also shown in the Appendix I).

It should be noted that the reported "NMR porosity" of the as-received cores in FIG. 3 and following plots is NMR liquid-filled porosity, while the "NMR porosity" of the saturated cores is the NMR total porosity. For 310, 320, 330, 340, 350, and 360, the porosities are 16.8, 18.3, 16.6, 12, 15.1, and 17.2 porosity units, respectively. The reported porosity assumes that all the detected fluids have a hydrogen index of unity, i.e. HI=1, which is the same as water. As such, the porosity values are listed in units of pu1, which is short for porosity units (pu) assuming HI=1. The reported NMR liquid-filled porosity or NMR total porosity follows a relationship with the actual porosities as such:

$$\phi_l(pu) = \frac{\phi_l(pu1)}{HI}, \quad (2)$$
$$\phi(pu) = \frac{\phi(pu1)}{HI},$$

where $\phi_l(pu)$ and $\phi(pu)$ are the actual liquid-filled and total porosity respectively, while $\phi_l(pu1)$ and $\phi(pu1)$ are the reported NMR liquid-filled porosity and NMR total porosity assuming HI=1, respectively. It should be noted that a large fraction of the bitumen signal with short $T_2$ due to its high viscosity is not detectible by the Geospec2. Therefore, the total porosity (i.e. NMR total porosity) reported in this study does not include the invisible portion of bitumen.

FIG. 3 indicates that the cores from the same depth have very similar $T_2$ distributions.

$T_2$ Distributions of Saturated Cores

Figure 4:
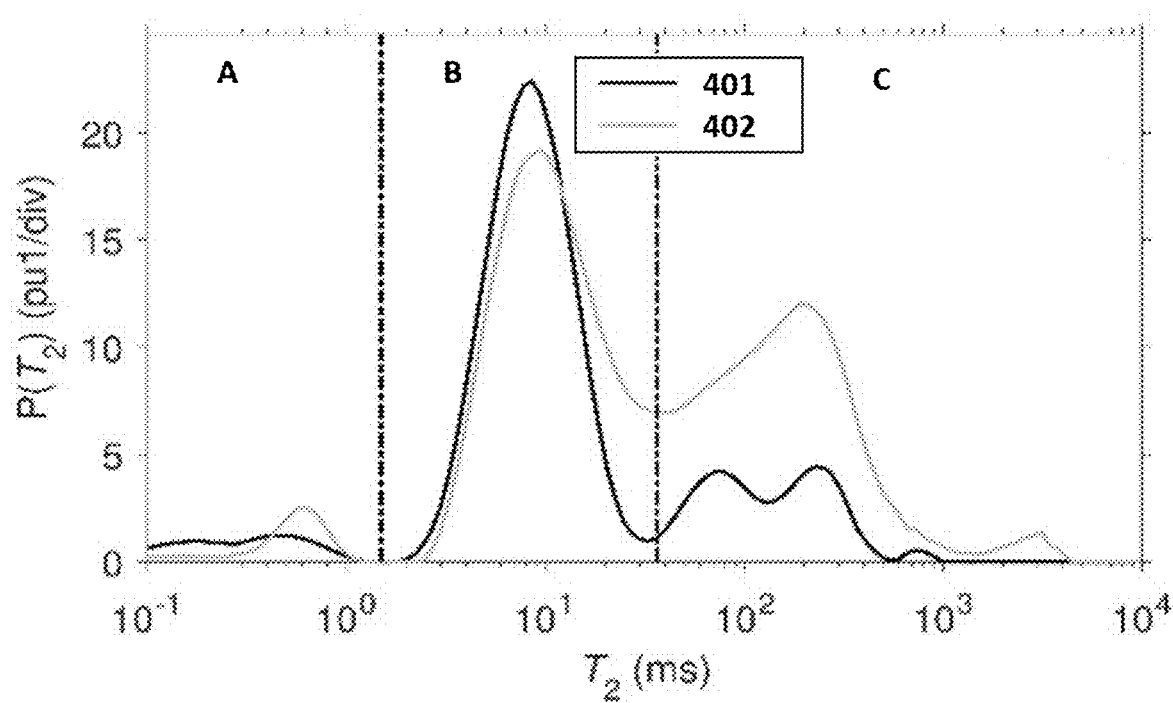
FIGS. 4-7 shows NMR $T_2$ distributions of as-received and fully-saturated cores.

Saturating the as-received cores in the laboratory is critical to study the NMR responses of different fluids (see Table 1 for saturation details). In this study, we use the water and hydrocarbons respectively to saturate the core under the laboratory conditions. The $T_2$ distribution acquired on the 100% water-saturated core provides the total NMR porosity. FIG. 4 presents the $T_2$ distribution of core No. 3 before (401) and after (402) water saturation. 401 has 16.9 porosity units, and 402 has 25 porosity units. It is clear there are around 8.1 porosity units of water introduced by water saturation. The fully water-saturated core measures a total NMR porosity of about 25 porosity units for all six "twin" cores.

Figure 5:
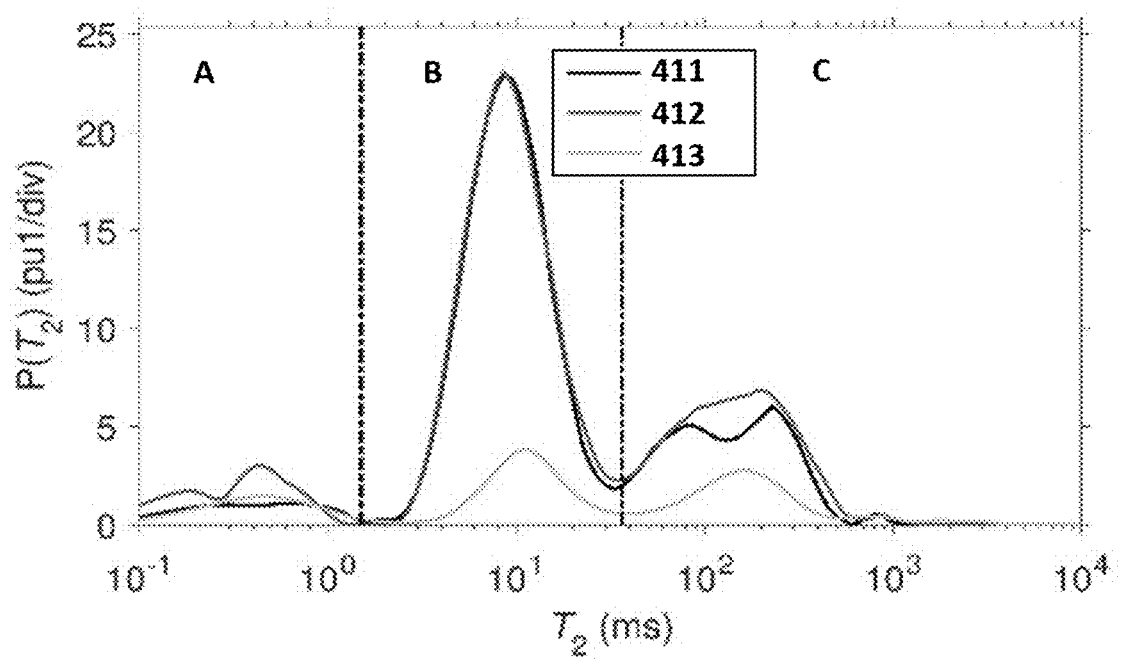
Figure 6:
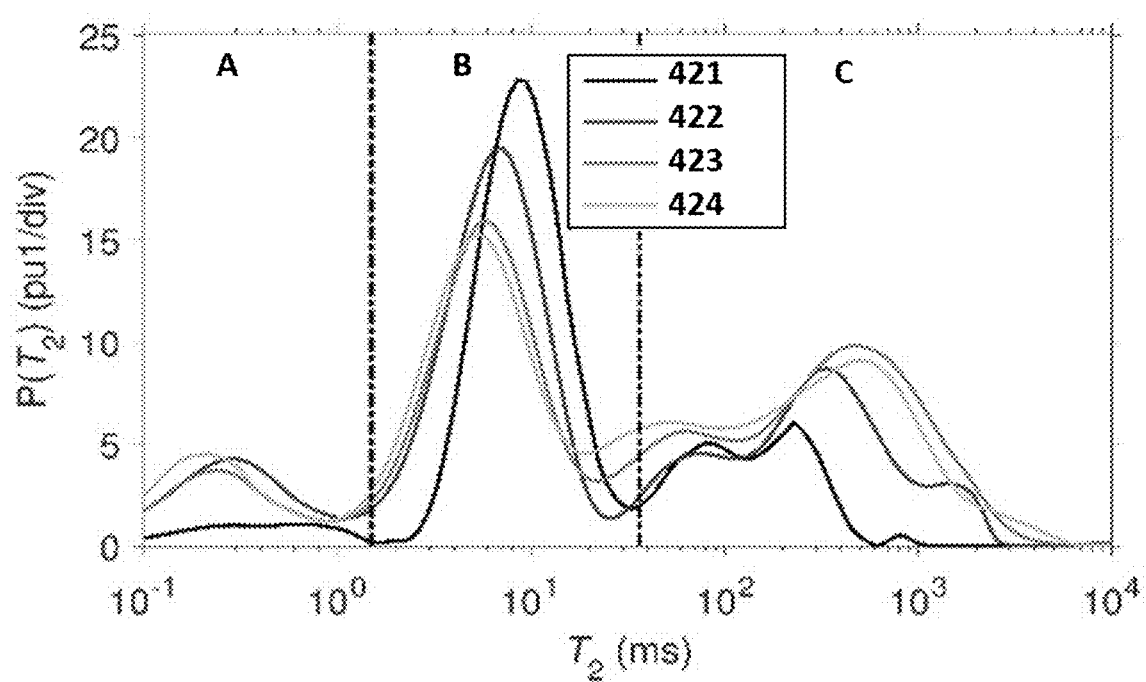
Figure 7:
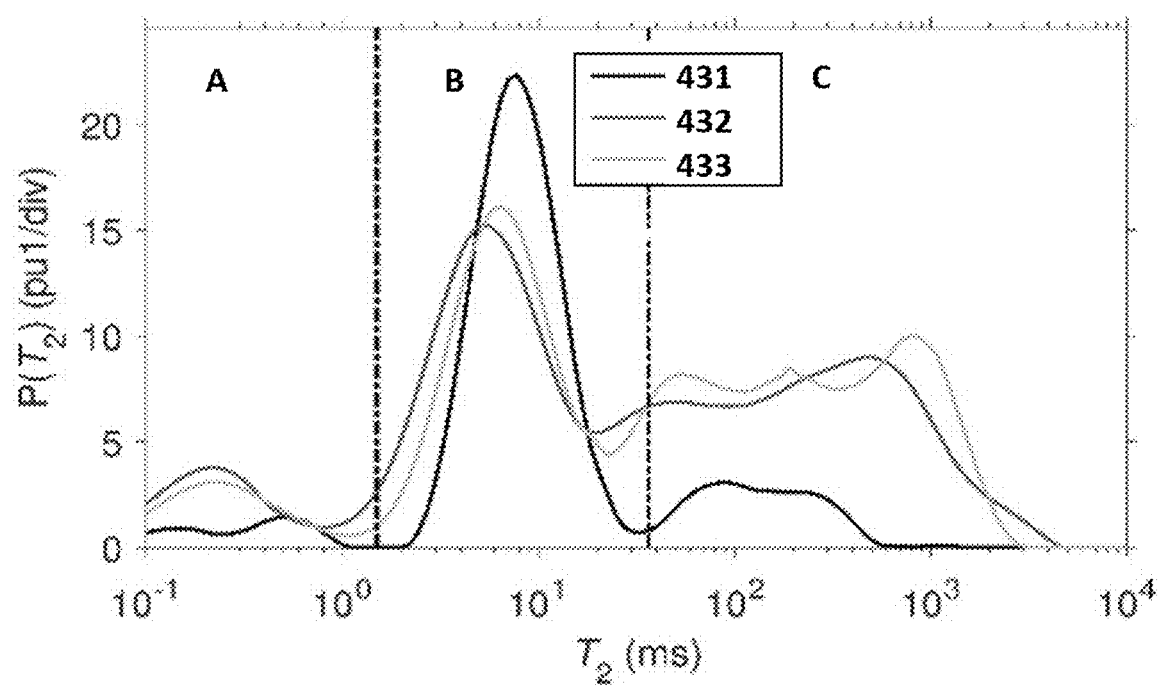

FIGS. 5, 6 and 7 provide $T_2$ distributions of hydrocarbons in the cores. In FIGS. 5, 411, 412, and 413 are core No. 2 before saturation (18.4 porosity units), core No. 2 saturated with methane (20.5 porosity units), and core No. 1 deuterated and saturated with methane (5 porosity units), respectively. In FIGS. 6, 421, 422, 423, and 424 are core No. 2 before saturation (18.4 porosity units), core No. 2 saturated with ethane (24.7 porosity units), core No. 1 saturated with propane (26.3 porosity units), and core No. 6 saturated with butane (26.9 porosity units), respectively. In FIGS. 7, 431, 432, and 433 are core No. 5 before saturation (15.7 porosity units), core No. 4 saturated with pentane (27.8 porosity units), and core No. 5 saturated with decane (27.7 porosity units), respectively.

The measurements illustrate different NMR porosity, especially in region C, which is due to the differences in HI between the hydrocarbons. Under laboratory conditions, methane is supercritical and yields a low HI of 0.13, while ethane, propane, butane, pentane, and decane are all liquids and yield much higher HI's (see Table 2). Since the HI of methane at reservoir conditions is twice that at laboratory conditions (also see Table 2), the simulated downhole $T_2$ response (shown below) must be compensated.

The total NMR porosity of water-saturated core in region A is slightly lower than that of pentane- and decane-saturated cores, even though water, pentane and decane share similar HI (see Table 2). This is interpreted as the dissolution of alkanes into either bitumen or kerogen, as suggested by the increase in signal intensity of region A after pentane and decane saturation (see FIG. 7).

In addition to the NMR porosity, there are other noticeable changes in $T_2$ distributions of the saturated cores. For the water-saturated core (No. 3), a slight increase in $T_2$ of connate water in region B is observed. This is because the connate water in micro pores in the micritic calcite (region B) is weakly diffusive-coupled with the water in the macro pores that are between the large grains of co-precipitated kerogen and calcite (region C). The diffusive coupling is weak because some bitumen clogging the pore throats limits the water exchange.

Since low-HI methane ("C1") only contributes a small amount of signal in region C indicated by FIG. 5, deuteration is useful when the methane response is analyzed. The $T_2$ of pure methane ("C1 (D2O)") in region C is the same as methane in the saturated core ("C1"), confirming that the extra signal seen on "C1" is not an artifact. It should be noted that the signal in region B of "C1 (D2O)" is due to water contamination because this part of the signal does not disappear after desaturation of methane, and also can be deuterated from the de-saturated core. The source of contamination may be from the moisture and remaining droplets of water (<0.5 mL) in the tubing and valves of the apparatus.

The $T_2$ response of ethane and longer alkanes in region C is separated into several peaks. The wettability may account for the distinct peaks. The pores for region C are located between the grains of co-precipitated kerogen and calcite. Therefore, the pores associated with region C are likely to be mixed wet. The longest $T_2$ of decane in region C is close to its bulk $T_2$ (about 3 s for deoxygenated decane). This may be because of a thin water film coating some surface of the mixed-wet pores, such that decane does not directly contact the pore walls. In such cases, the surface relaxation of decane is provided by the decane-water interface instead of the decane-solid interface. It can be expected that the surface relativity of the decane-water interface is much smaller compared to the decane-solid interface. Hence, decane contacting with kerogen solid surface may yield shorter $T_2$ that is distinct from the bulk $T_2$. The same interpretation applies to other alkanes that have distinct peaks in region C.

$T_{2app}$ Distributions and Composition Estimation

Due to their magnetic-field gradients, gradient-based NMR logging tools measure the "apparent" $T_2$ relaxation, defined as $T_{2app}$ and given by:

$$\frac{1}{T_{2app}} = \frac{1}{T_2} + \frac{1}{T_{2D}}, \quad (3)$$

$T_2$ is the transverse relaxation time without applied magnetic-field gradients, as reported in the previous subsections. $T_2D$ is the additional term due to fluid diffusion in an applied magnetic-field gradient generated by the logging tool as such:

$$\frac{1}{T_{2D}} = \frac{\gamma^2 G^2 T_E^2 D}{12}, \quad (4)$$

Figure 8:
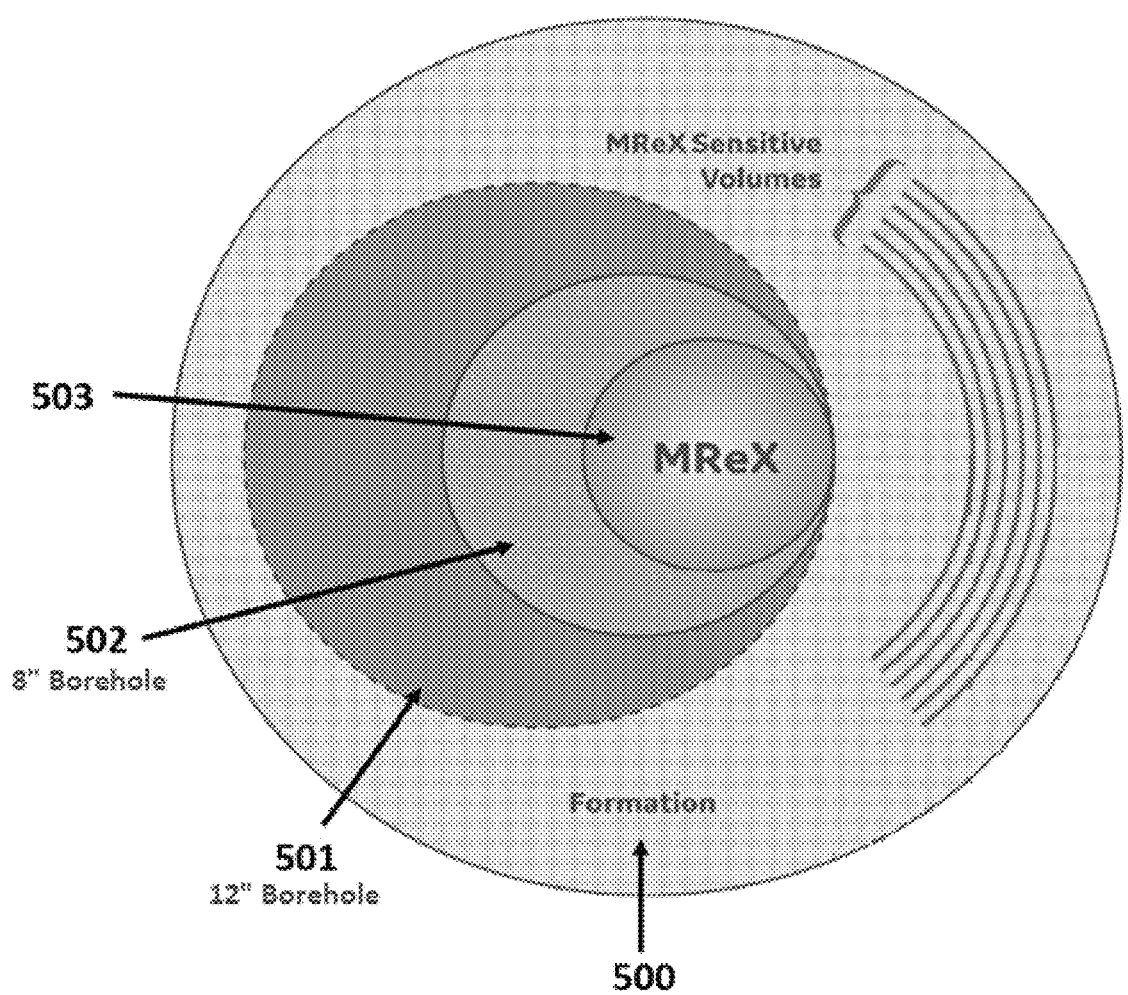
FIG. 8 shows a downhole gradient-based NMR logging tool in a borehole.

$\gamma/2\pi$=42.58 MHz/T is the gyromagnetic ratio of proton. The Baker Hughes MREX NMR logging tool used in this example has an echo spacing $T_E$ of 0.4 ms. G is the magnetic-field gradient applied by the NMR logging tool. The MREX NMR logging tool provides six equal sensitive volumes with G's of 17.0, 22.0, 23.4, 27.4, 32.7 and 38.7 G/cm respectively. A diagram of the MREX logging tool 503 in an 8" (502) and 12" (501) borehole is shown in FIG. 8. The MREX sensitive volumes are located between 2.1 and 3.8 inches into the formation 500.

D represents the diffusivity of hydrocarbons, where the restricted diffusivities under logging conditions are used. This is detailed in the following section on NMR restricted diffusion measurements using a Padé fit. Restricted diffusivities are used because the diffusion lengths of fluids, especially that of methane, are close to the pore diameter, which means the fluids experience restriction from the limited pore space. Note that in the cases where restriction is negligible (i.e. pore diameter is much greater than the diffusion length), the bulk diffusivity of fluids can be used to calculate the magnetic-field gradient effect, which leads to simpler implementation of this invention.

Other gradient-based NMR logging tools could be used within the scope of this invention, such as the Schlumberger MRX or the Halliburton MRIL.

Figure 9:
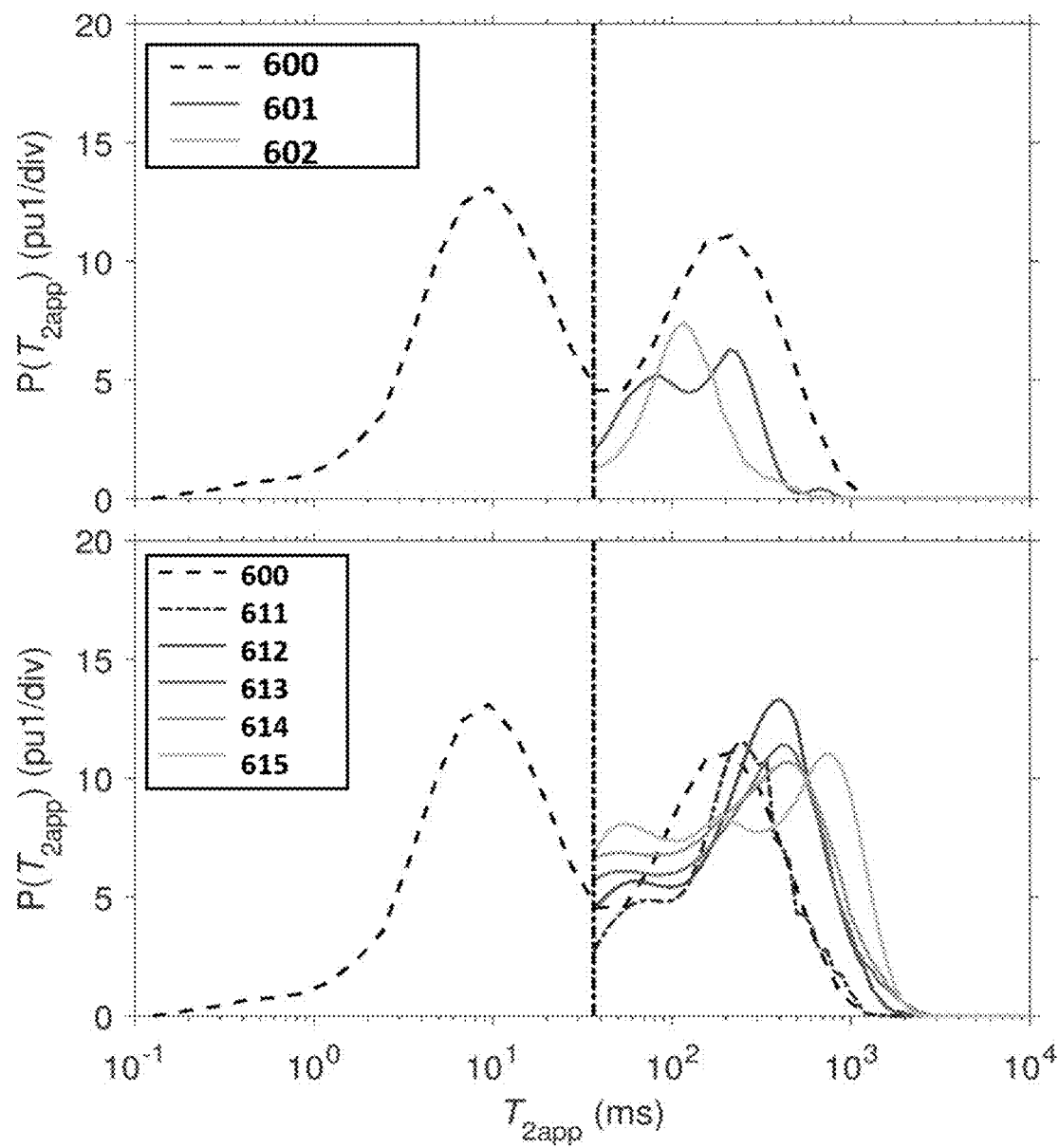
FIG. 9 shows a comparison of incremental $T_{2app}$ distribution from downhole NMR log and simulated $T_{2app}$ distribution based on laboratory-measured data.

For core-log comparison, the extra $T_{2D}$ term is added to the laboratory-measured $T_2$ distributions. In addition, the first echo (at 0.2 ms) of the time-domain raw data for the laboratory measurements is dropped to match the first echo time of the logging tool. Note that increasing the echo spacing in the laboratory measurement to 0.4 ms had no impact on the $T_2$ distributions in regions B and C, implying no internal gradient effects at 2 MHz. The simulated $T_{2app}$ is re-scaled by the HI of fluids, which means the porosity in the $T_{2app}$ distribution of methane is boosted by a factor of two because of the difference in HI under reservoir and laboratory conditions (see Table 2). As for longer alkanes and water, the effect of re-scaling is insignificant because those fluids share similar HI at both conditions. FIG. 9 presents the $T_{2app}$ distribution from the downhole log and the $T_{2app}$ distributions from the as-received (i.e. with connate-water saturated) and hydrocarbon-saturated cores simulated based on the laboratory measurements. Note that for simulated $T_{2app}$ distributions only region C is shown. The log data are acquired at the same depth where the as-received plugs were cored. The two subplots share the same log data. The simulated $T_{2app}$ distribution has the HI difference under different conditions compensated. The dashed vertical lines separate region C from the other two regions. The upper subplot of FIG. 9 shows the log data (10.6 porosity units) 600, corresponding core before saturation (4.7 porosity units) 601, and after deuteration and saturation with methane (3.8 porosity units) 602. The lower subplot of FIG. 9 shows the log data 600, saturation with ethane (8.7 porosity units) 611, propane (11.7 porosity units) 612, butane (11.5 porosity units) 613, pentane (12.3 porosity units) 614, and decane (13.5 porosity units) 615.

Introducing the $T_{2D}$ term to laboratory—measured $T_2$ has no impact on regions A and B where $T_2$ is much shorter than $T_{2D}$. However, introducing the $T_{2D}$ term leads to shorter relaxation time $T_2$ in region C, with narrower and higher peaks. It is found that methane has shorter $T_{2app}$ than the log, while longer alkanes have higher $T_{2app}$ than the log; therefore, a combination of the hydrocarbons is expected to match with the log.

To determine the composition of light hydrocarbons in the reservoir, the $T_{2app}$ distributions of light hydrocarbons in the core are numerically mixed in data post-processing, by averaging their $T_{2app}$ distributions weighted by different volume fractions. This analysis assumes that hydrocarbons yield the same $T_{2app}$ distribution in the mixture as they would in single component form (i.e. the $T_{2app}$ distributions are linearly additive). It is also assumed that, in the ethane- and higher alkane-saturated core, the signal of region C is from hydrocarbons with negligible amount of connate water (i.e. only thin water films coating the water-wet portions of pores but not contributing to the signal intensity). This is suggested by measurements on de-saturated cores, of which the $T_2$ distributions provide nearly zero signal in region C, except for methane. In the case of methane, "C1 (D2O)" is used instead of "C1" for "numerical mixing" because "C1 (D2O)" is measured after the propane experiment where the connate water in region C was expelled by propane. Hence, "C1 (D2O)" presents the $T_{2app}$ distribution when methane occupies the entire pore space of region C.

The "numerical mixing" of $T_{2app}$ makes use of the $T_{2app}$ of the "As-Received" cores as the baseline to represent the connate water in the reservoir. The $T_{2app}$'s of hydrocarbons are added to the "As-Received" after being multiplied by the total hydrocarbon saturation of region C and the volume fraction (i.e. composition) of individual hydrocarbon. The total light hydrocarbon saturation in region C is about 65% since the connate-water saturation is 4.7 pu/13.5 pu≈35%. Note that the NMR porosity of the fully decane-saturated (instead of water-saturated) core is adopted for the above saturation calculation because water in macro pores (region C) is diffusively-coupled to water in micro pores (region B), which leads to shorter $T_{2app}$ and less NMR porosity for region C.

A search algorithm is implemented to determine the optimal volume fraction of hydrocarbons that minimizes the mean square error MSE (i.e., sum of the squares of the deviations) between "numerically mixed" $T_{2app}$ distribution and the log for region C where $T_{2app} \geq 36.6$ ms.

Figure 10:
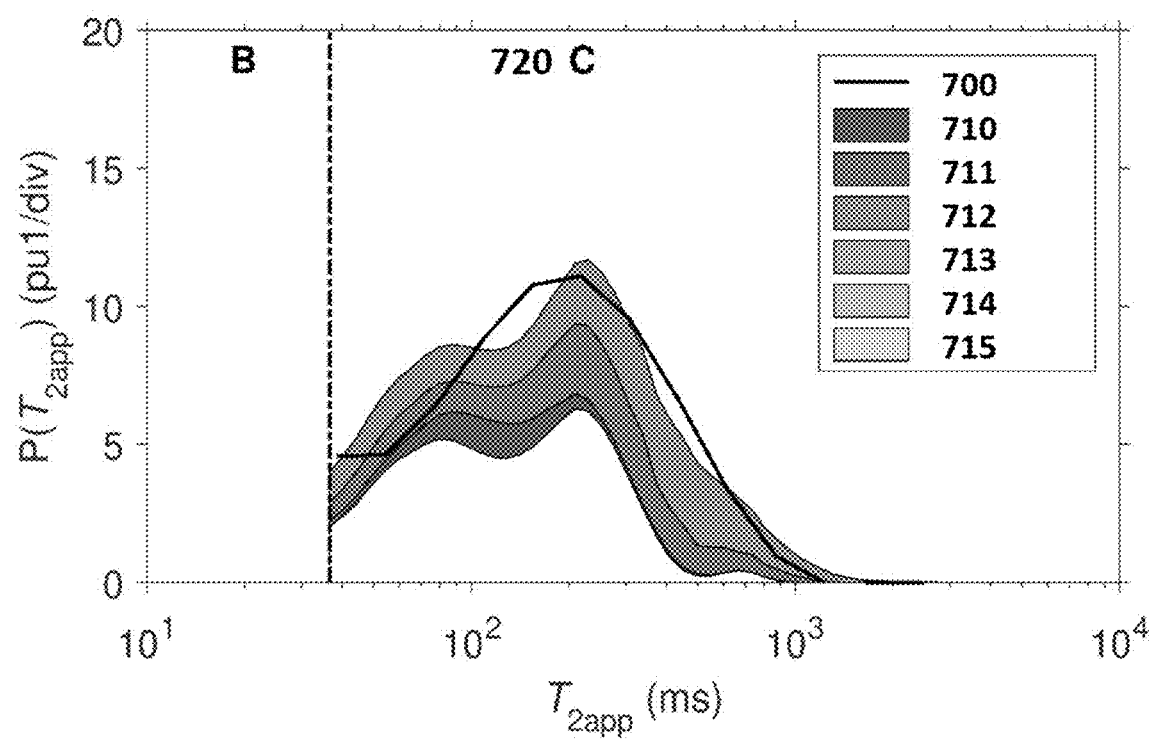
FIG. 10 shows a comparison of incremental $T_{2app}$ distributions from downhole NMR log and numerically mixed hydrocarbons saturated core.

The optimal volumetric fractions of hydrocarbons obtained by the search are shown in FIG. 10. In FIG. 10, the $T_{2app}$ distributions of hydrocarbons in the mixture are broken down to single components with grayscale color scheme to visualize the composition. The total gray-colored area denotes the light hydrocarbon-filled porosity. The outline of the gray-colored area denotes the final $T_{2app}$ distributions of the mixture. The white area under the gray colored areas is associated with connate water. The dashed vertical line indicates the $T_{2app}$ above the region C cutoff that is searched to find the optimal volumetric fraction.

The optimal volumetric fraction of the mixture is illustrated in the legend. 700 is the log response, while 710 (methane, 27 vol %), 711 (ethane, 36 vol %), 712 (propane, 37 vol %), 713 (butane, 0 vol %), 714 (pentane, 0 vol %), and 715 (decane, 0 vol %) are the optimal volumetric fraction of hydrocarbons that fit the log. It is obvious that butane (713), pentane (714), and decane (715) do not contribute to the optimal mixture. Methane contributes about 27%, ethane 36% and propane 37% to the mixture. By converting the volumetric fraction to porosity units, the total fluid-filled porosity of the three hydrocarbons is 8.8 pu. Methane, ethane and propane occupy approximately 2.4, 3.2, and 3.2 pu respectively. The NMR porosity units are given with the assumption that HI=1.

The ratios of C2/C1, C3/C1, and C2/C3 as well as other ratios like (C2+C3+C4)/C1 may be computed from this data.

Because of linear additivity, the fluid compositions used in saturating the cores can themselves be mixtures of the pure alkanes, (e.g. 50% C2 and 50% C3) if the compositions of the mixtures are known. This is included within the scope of this invention.

It is also within the scope of this invention to saturate the core with the volumetric mixture of C1-C5 that has been determined to be the optimal mixture at reservoir conditions, then make the laboratory NMR measurements at reservoir conditions, and compare the laboratory NMR measurements with the downhole NMR log. This can be done as a final verification step.

Although, in this example chalk formation, region C (720) containing light hydrocarbons starts at $T_{2app} \geq 36.6$ ms, in other formations it may start at other values, such as 30, 20, or 10 ms.

Figure 11:
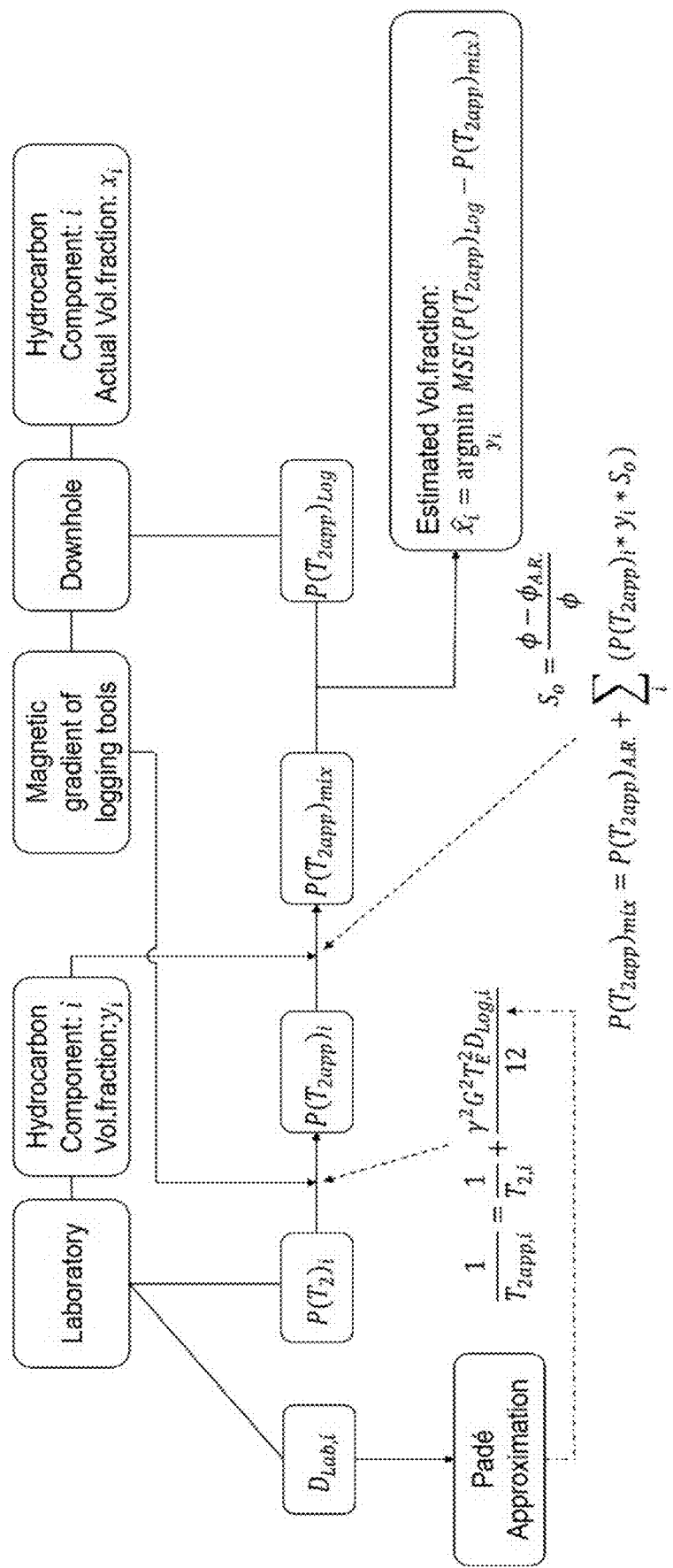
FIG. 11 is a detailed workflow used for numerical mixing.
Figure 12:
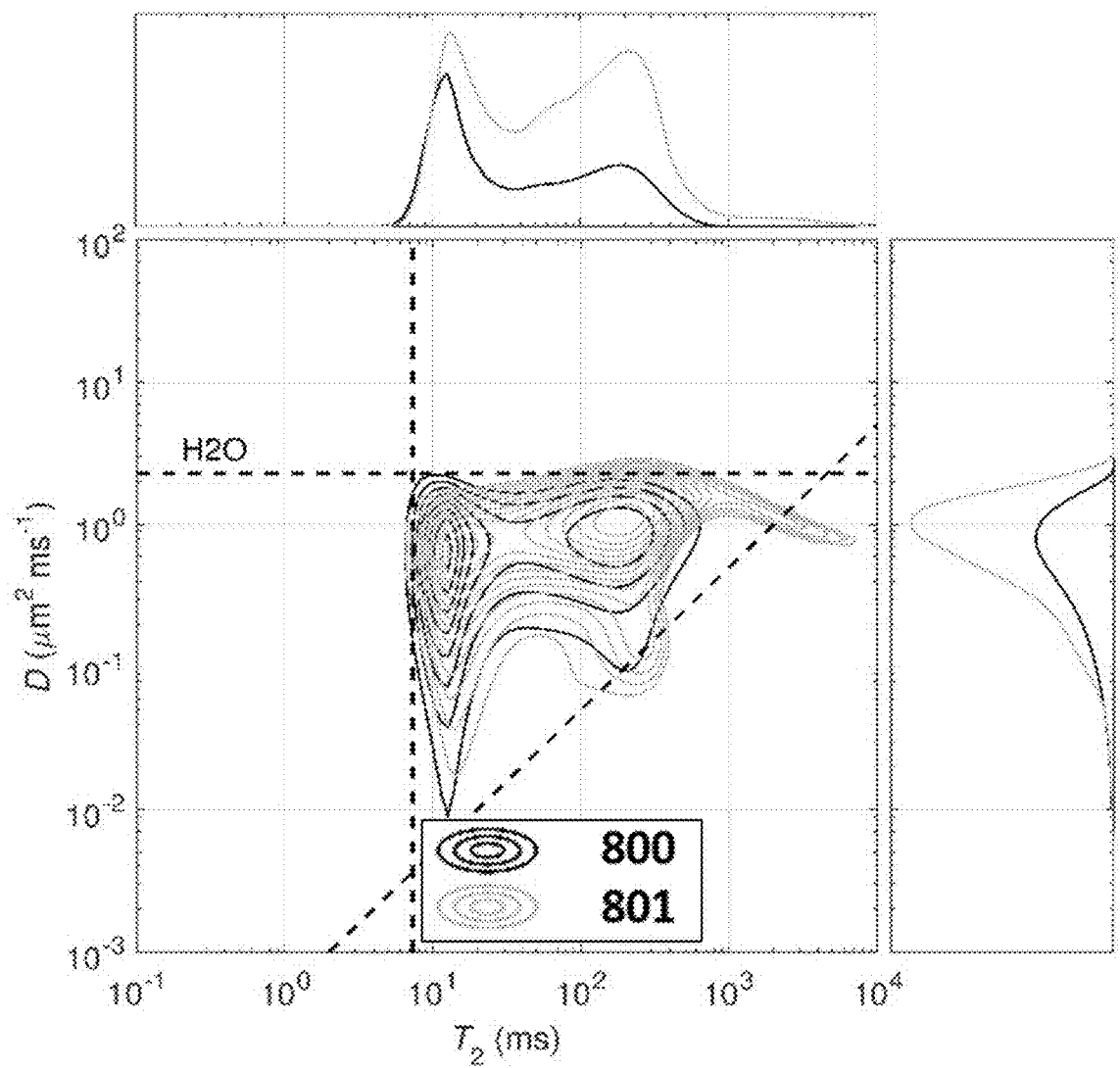
FIGS. 12-15 are 2-D correlation maps of as-received and saturated cores.
Figure 13:
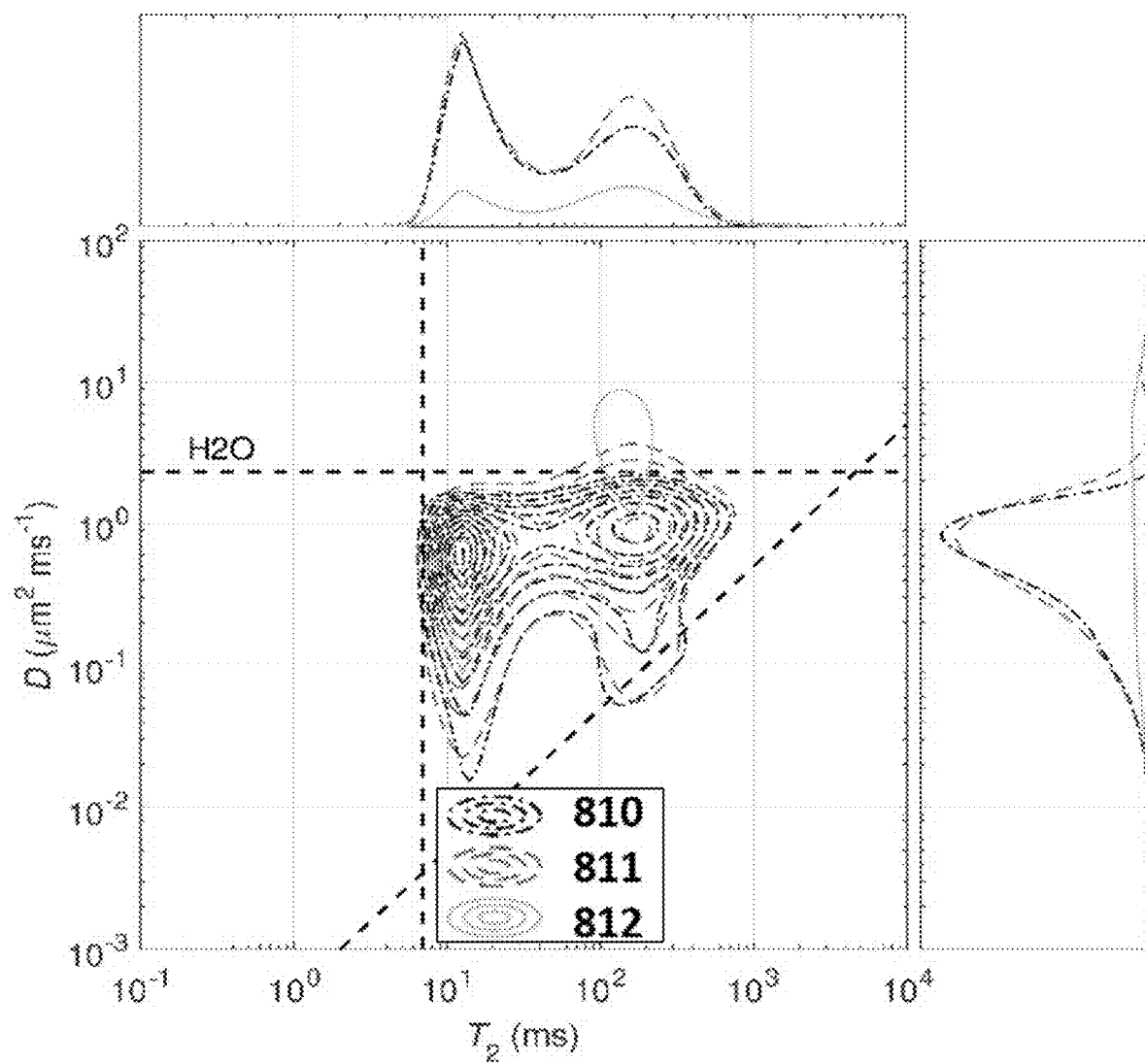
Figure 14:
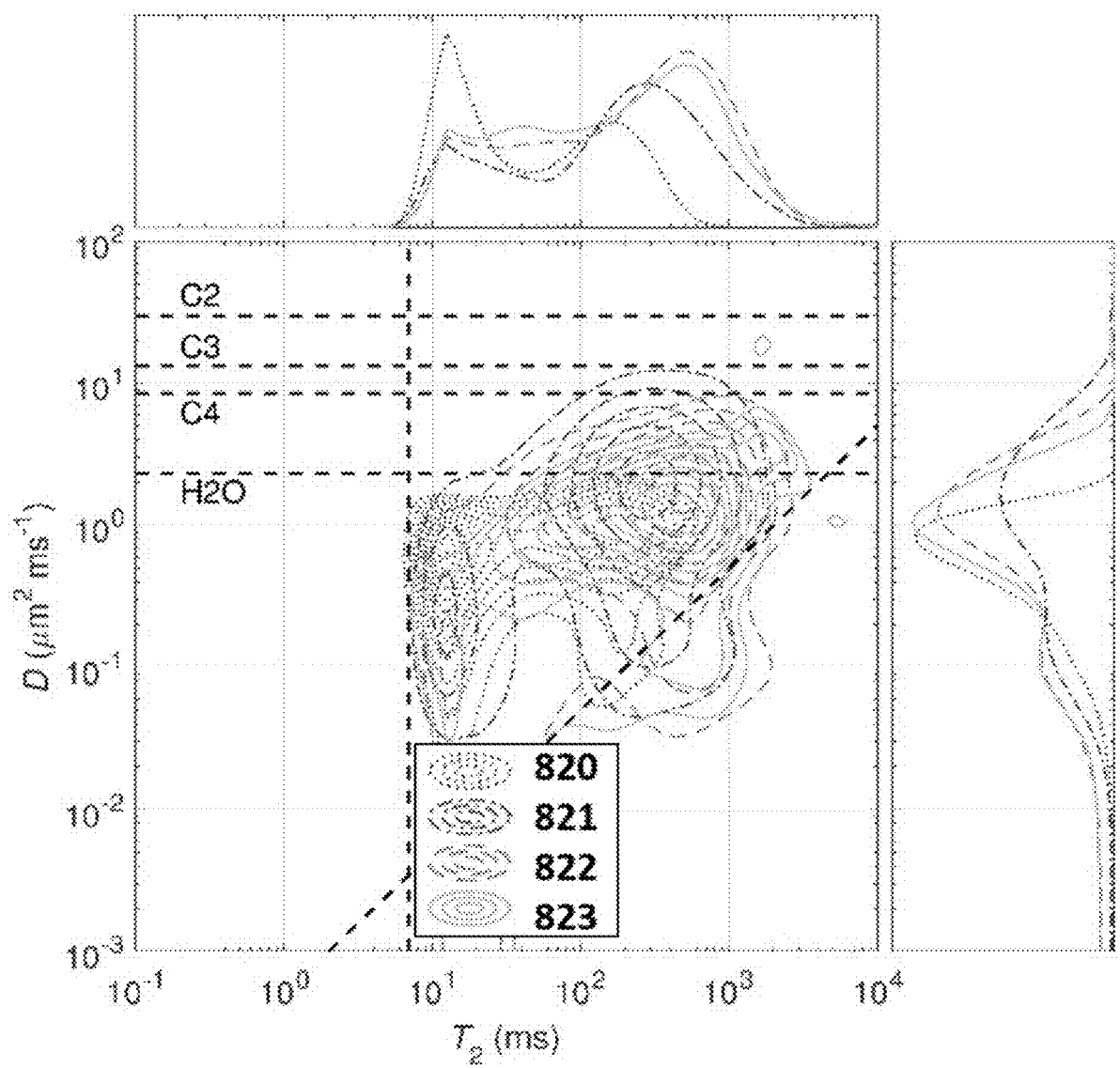
Figure 15:
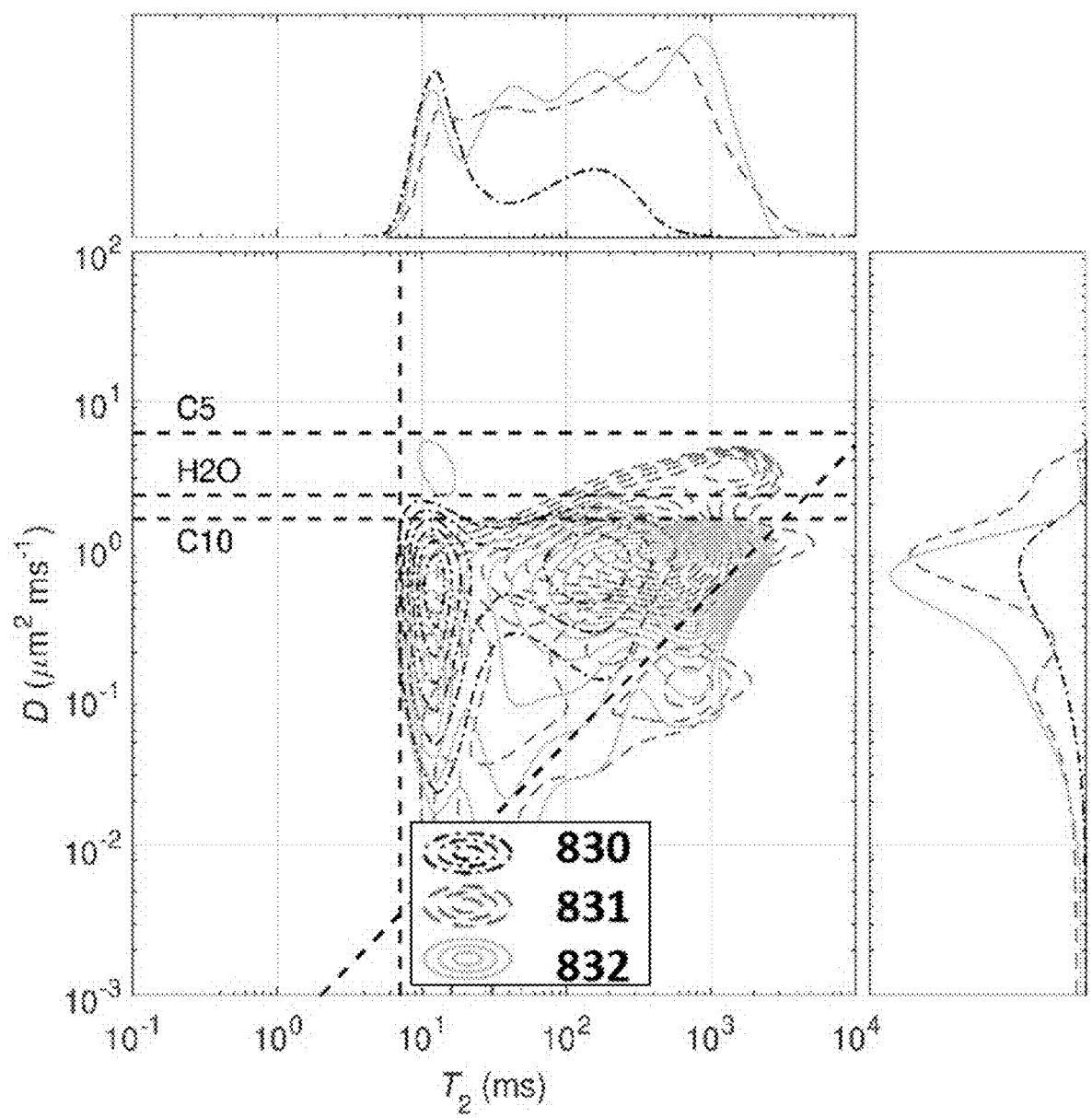

FIG. 11 summarizes the workflow used in this invention for numerical mixing. MSE is the mean square error. The following section on restricted diffusion provides additional details.

Restricted Diffusion and Pore Size

This section presents $D$-$T_2$ measurements conducted in the laboratory on as-received and saturated cores to measure restricted diffusion of the fluids in the core. The diffusivities of light hydrocarbons are fitted to the Padé approximation to estimate the mean pore-size, the heterogeneity length scale, and the tortuosity of the light hydrocarbon-filled porosity.

$D$-$T_2$ Measurements

FIGS. 12-15 show the measurements of restricted diffusion on the cores at different states. These are 2-D correlation maps of the as-received and saturated cores discussed in FIGS. 4-7, with D (diffusivity) on the y-axis, $T_2$ on the x-axis, and porosity contours perpendicular to the page. For each figure, the top subplot is the projected $T_2$ distribution. The right subplot is the project D distribution. The dashed black horizontal lines are the bulk diffusivity of the fluids (labeled next to the lines) in laboratory conditions except for methane (which is out of range of the y-axis). The dashed black diagonal line is the alkane correlation line (Lo et al., 2002). The dashed black vertical line is to indicate the limitation from dead time inherent in the diffusion-encoding pulse sequence. Generally, the 2-D D-$T_2$ measurements are challenging due to the short $T_2$ of tight rocks. For the unipolar stimulated-echo sequence (Mitchell et al., 2014) adopted here, the dead time $T_d$=25 ms required to encode diffusion also acts as a dead time for $T_2$ measurement, which results in loss of signal below $T_2$<7 ms (signal intensity attenuated to 5%, indicated by the dashed vertical line in FIGS. 12-15). The dead time $T_d$ is composed of two parts as:

$$T_d = \Delta + \delta, \quad (5)$$

where $\Delta$ is the diffusion evolution time (a.k.a. observation time) and $\delta$ is the gradient encoding time. During the laboratory NMR measurements, $\Delta$=14.7 ms and $\delta$=9 ms. In this example, the $T_2$ from region A and B are mostly less than 7 ms where the diffusion measurement is limited, even though a small portion of region B can be seen. However, the signal from region C which contains the light hydrocarbons can be measured without significant loss. The restricted diffusivity at the peak of region C was picked for later analysis (see the following subsection on interpretation of restricted diffusion).

FIGS. 12-15 show that the measured diffusivities are all less than bulk values due to the restriction in the porous medium. Because of the interference from connate water, the 2-D distribution in region C of liquid hydrocarbons are broad. Note that the bulk diffusivity of methane is around 250 μm²/ms, which is out of range of y-axis in the 2-D correlation map. Pure methane ("C1 (D2O)") in FIG. 5 generates a small peak with higher diffusivity which cannot be observed while connate-water signal is present. It is also found that decane ("C10") follows the alkane correlation line proposed by Lo et al., 2002.

Interpretation of Restricted Diffusion

Figure 16:
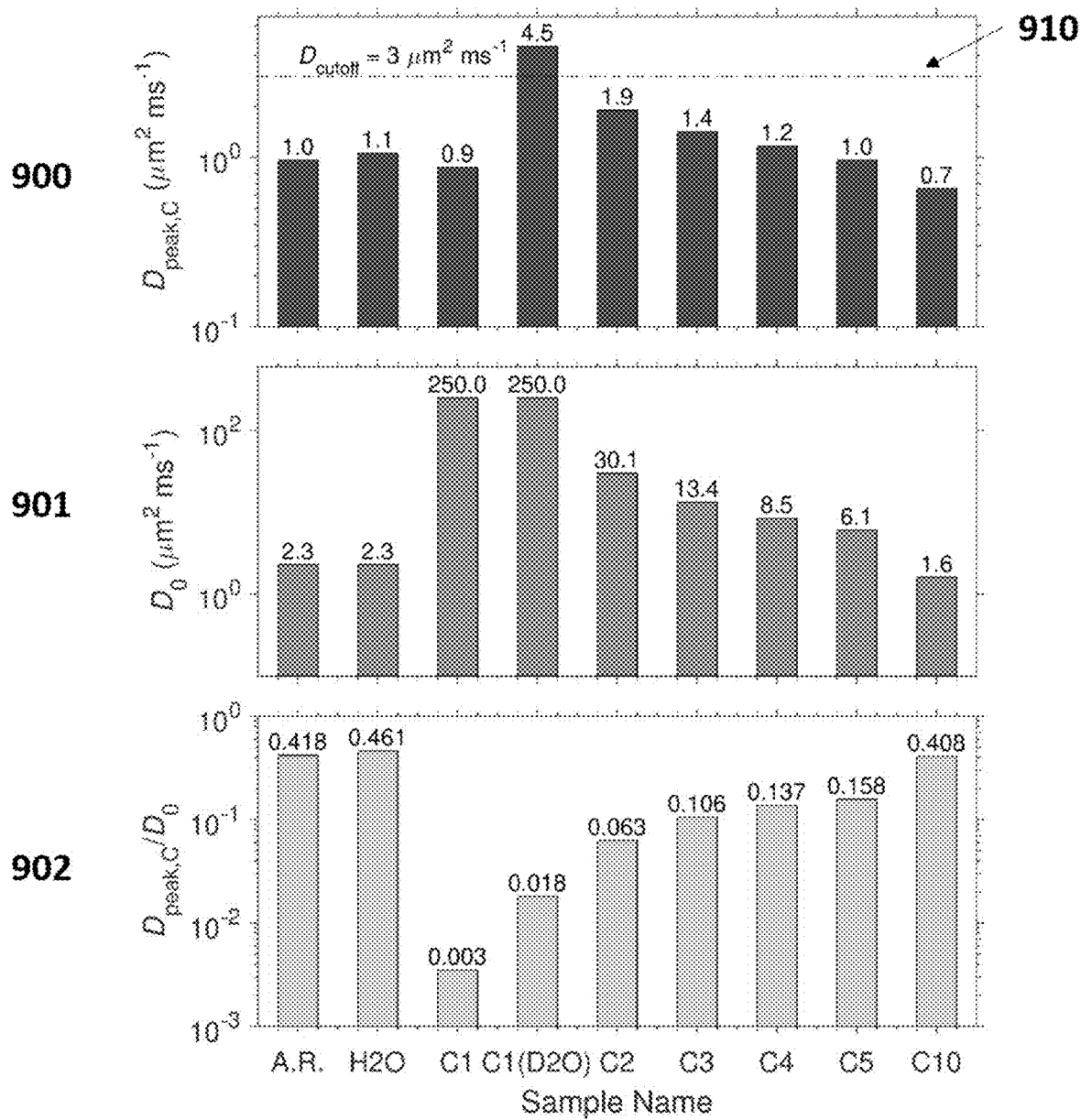
FIG. 16 shows laboratory-measured restricted diffusivity at the peak of region C, bulk diffusivity (in laboratory conditions), and normalized restricted diffusivity with respect to the bulk diffusivity.

FIG. 16 compares laboratory-measured restricted diffusivity at the peak of region C (top subplot, 900), bulk diffusivity under laboratory conditions (middle subplot, 901), and normalized restricted diffusivity with respect to the bulk diffusivity (bottom subplot, 902). The y-axis shows the diffusivity, and the x-axis indicates either connate water (as-received) or saturating fluids.

The normalized restricted diffusivity is a function of the restriction experienced during the diffusion evolution time. Water and decane share similar bulk diffusivity, therefore almost the same amount of restriction (i.e., the same normalized restricted diffusivity). In contrast, methane and NGLs have much higher bulk diffusivities, and therefore more restriction (i.e. lower values of normalized restricted diffusivity compared with water or decane). Furthermore, the restriction experienced by hydrocarbons becomes less as the carbon number increases (e.g. as bulk diffusivity decreases). The measured restricted diffusivity of methane suggests that a cutoff of 3 µm²/ms (indicated by the horizontal dashed line 910 in the top subplot of FIG. 16) can be implemented to separate the methane, which is the only supercritical hydrocarbon, from the other liquids in the laboratory diffusion measurements. Note that the extremely small value of the normalized restricted diffusivity indicates methane is highly restricted and approaching the tortuosity limit.

Figure 17:
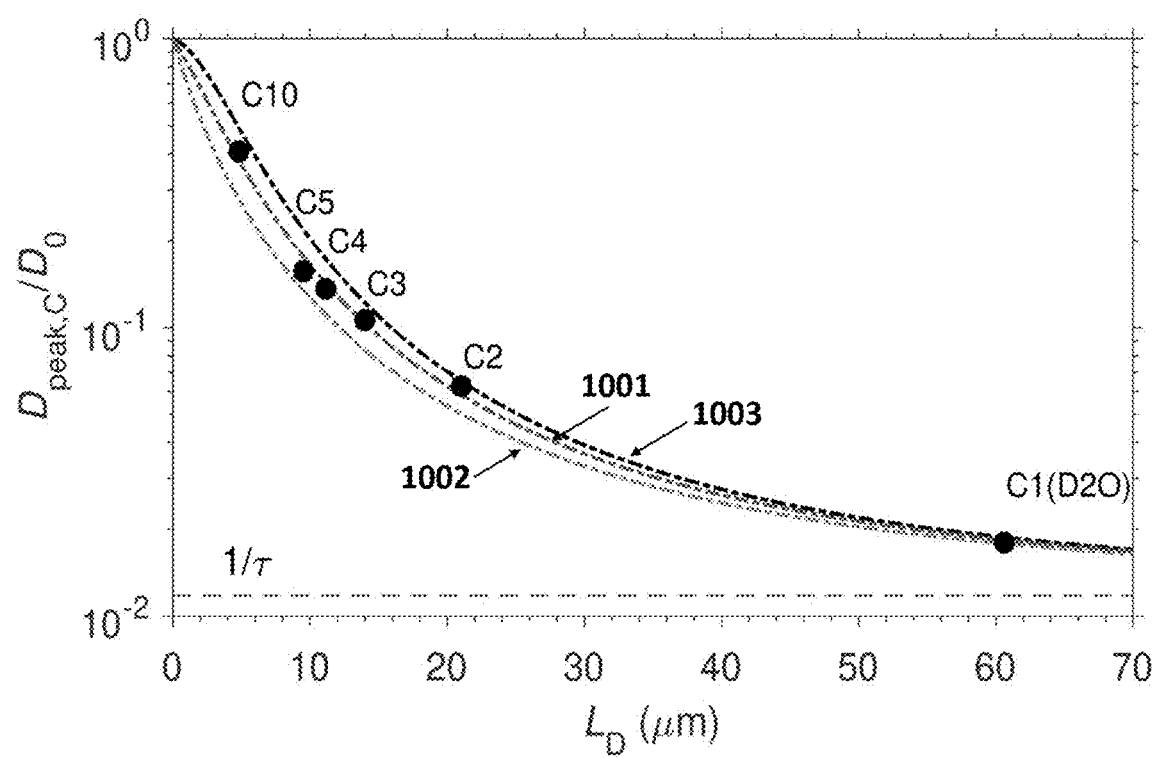
FIG. 17 shows normalized restricted diffusivity plotted against diffusion length $L_D$.

In FIG. 17, the normalized restricted diffusivity of different hydrocarbons is plotted against diffusion length $L_D$ calculated by Equation 6:

$$L_D = \sqrt{D_0 \Delta}, \quad (6)$$

where $D_0$ is the bulk diffusivity on laboratory conditions and $\Delta = 14.7$ ms is the diffusion evolution time. Based on the Padé approximation, Hürlimann et al., 1994 suggests that the normalized restricted diffusivity $D/D_0$ follows a relationship with diffusion length $L_D$ as in Equation 4:

$$\frac{D}{D_0} = 1 - \left(1 - \frac{1}{\tau}\right) \frac{\frac{4}{9\sqrt{\pi}} \frac{S}{V} L_D + \left(1 - \frac{1}{\tau}\right) \frac{L_D^2}{L_M^2}}{\frac{4}{9\sqrt{\pi}} \frac{S}{V} L_D + \left(1 - \frac{1}{\tau}\right) \frac{L_D^2}{L_M^2} + \left(1 - \frac{1}{\tau}\right)}, \quad (7)$$

S is the pore surface area and V is the pore volume, and we assume spherical pores that yield $S/V \approx 3/r_p$, where $r_p$ stands for the pore radius of the hydrocarbon-filled space in region C. $\tau$ is the tortuosity of the hydrocarbon-filled space in region C, and can be expressed by Equation 5:

$$\tau = \frac{D_0}{D_\infty} \quad (8)$$

$D_\infty$ is the diffusivity at the tortuosity limit. $L_M$ is the macroscopic heterogeneity length scale. It should be noted that in the model suggested by Latour et al. 1993, $L_M$ is expressed by $(D_0 \theta)^{1/2}$, where $\theta$ is the fitting parameter for a fluid. However, since there are different fluids with various $D_0$ in this invention, the $L_M$ is used as the overall fitting parameter, which means $\theta$ changes to accommodate different fluids.

According to the above model, there is a total of three free parameters: $r_p$, $\tau$ and $L_M$. A least-square fit based on this model is applied to the $\log_{10}$—transformed restricted diffusivity shown in FIG. 17. The final fit (1001) is presented in FIG. 17 with $r_p = 4.6$ µm, $L_M = 5.1$ µm and $\tau = 84.9$ as the optimized parameters. Another two curves are plotted by changing $r_p$ to 2 µm (1002) and 20 µm (1003), along with the final fit (1001) to demonstrate the sensitivity of this model to different pore size. The sensitivity analysis suggests this approach can be applied to estimate the pore size $r_p \leq 5$ µm with relatively high resolution.

Another hydrogen-bearing fluid that can be included in FIG. 17 is hydrogen gas, $H_2$. Hydrogen gas has much higher diffusivity than methane and therefore longer $L_D$. Measurements using hydrogen gas would be substantially closer to the $1/\tau$ tortuosity limit and therefore help determine the tortuosity more accurately if added to the group of hydrocarbons in FIG. 17.

It should be noted that the original model proposed by Hürlimann et al., 1994 is for the case of 100% saturation and 100% wetting. Minh et al., 2015 suggests the equation should be changed accordingly if the investigated case is not 100% saturation nor 100% wetting. In this invention, only the hydrocarbon-filled porosity (region C) is considered. Therefore, the original model by Hürlimann et al., 1994 is adopted in this invention. It is within the scope of this invention that other numerical models could also be used.

The macroscopic heterogeneity length scale $L_M$ is 5.1 µm, which is close to the mean pore radius of 4.6 µm. Empirically the $L_M$ should scale with mean pore-size as suggested by Latour et al., 1993 and Hürlimann et al., 1994.

According to the Padé fit acquired in the laboratory conditions, the restricted diffusivities experienced by fluids during downhole logging can be determined by extrapolating the Padé fit to the downhole diffusion length $L_D$. To achieve this, the bulk diffusivity $D_0$ in laboratory conditions in Equation 4 is replaced by the bulk diffusivity in the reservoir conditions (as illustrated in the top subplot of FIG. 17). Bulk values of fluids at both laboratory and targeted reservoir conditions are shown in Table 2.

In addition, the diffusion evolution time in Equation 5 is changed to echo spacing $T_E = 0.4$ ms for the NMR logging tool instead of $\Delta = 14.7$ ms for the laboratory NMR core analyzer.

Figure 18:
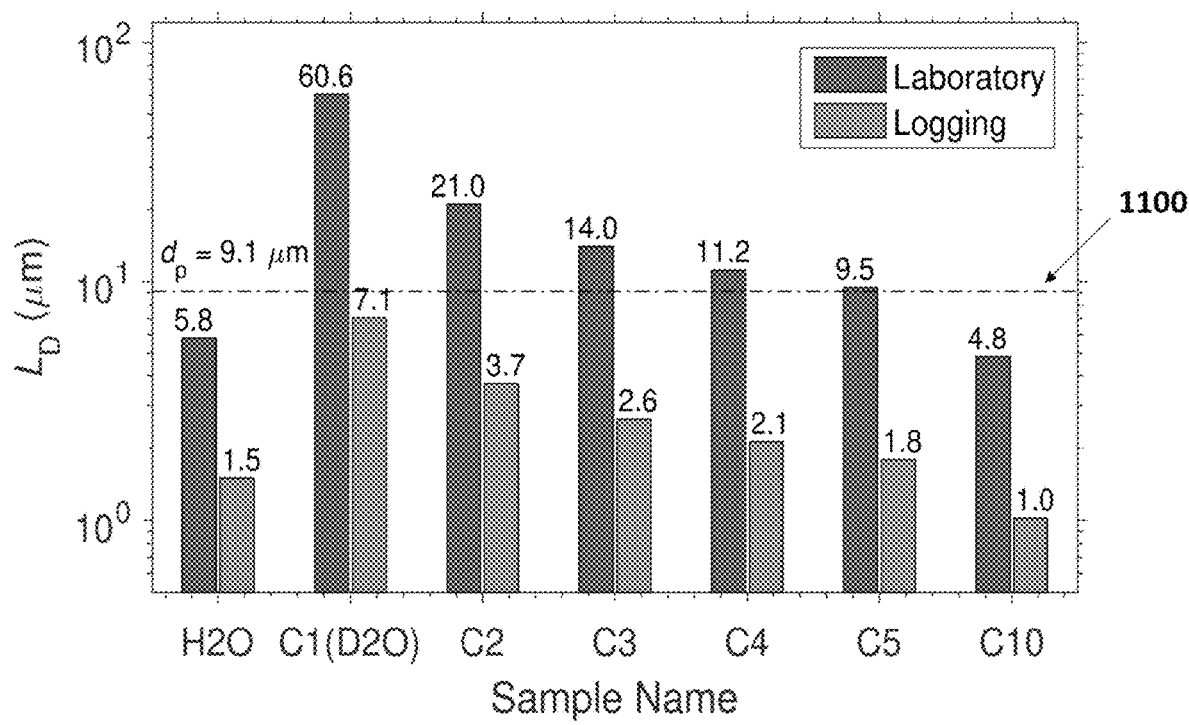
FIG. 18 is a comparison of the diffusion lengths of saturating fluids during D-$T_2$ laboratory measurements.

The diffusion lengths for logging conditions ($T_{2app}$) are plotted in FIG. 18 along with those at laboratory conditions (D-$T_2$ measurements) for comparison. The pore diameter estimated by the Padé fit is also plotted as the dashed line 1100. Note that the diffusion length of methane at logging conditions is close to the pore diameter, such that methane experiences restricted diffusion. The restriction decreases as the diffusion length decreases. The restriction for the hydrocarbon fluids other than methane are less significant, as suggested by the Padé fit, but still not negligible. This is the reason why the restricted diffusivity is used in place of the bulk diffusivity.

Figure 19:
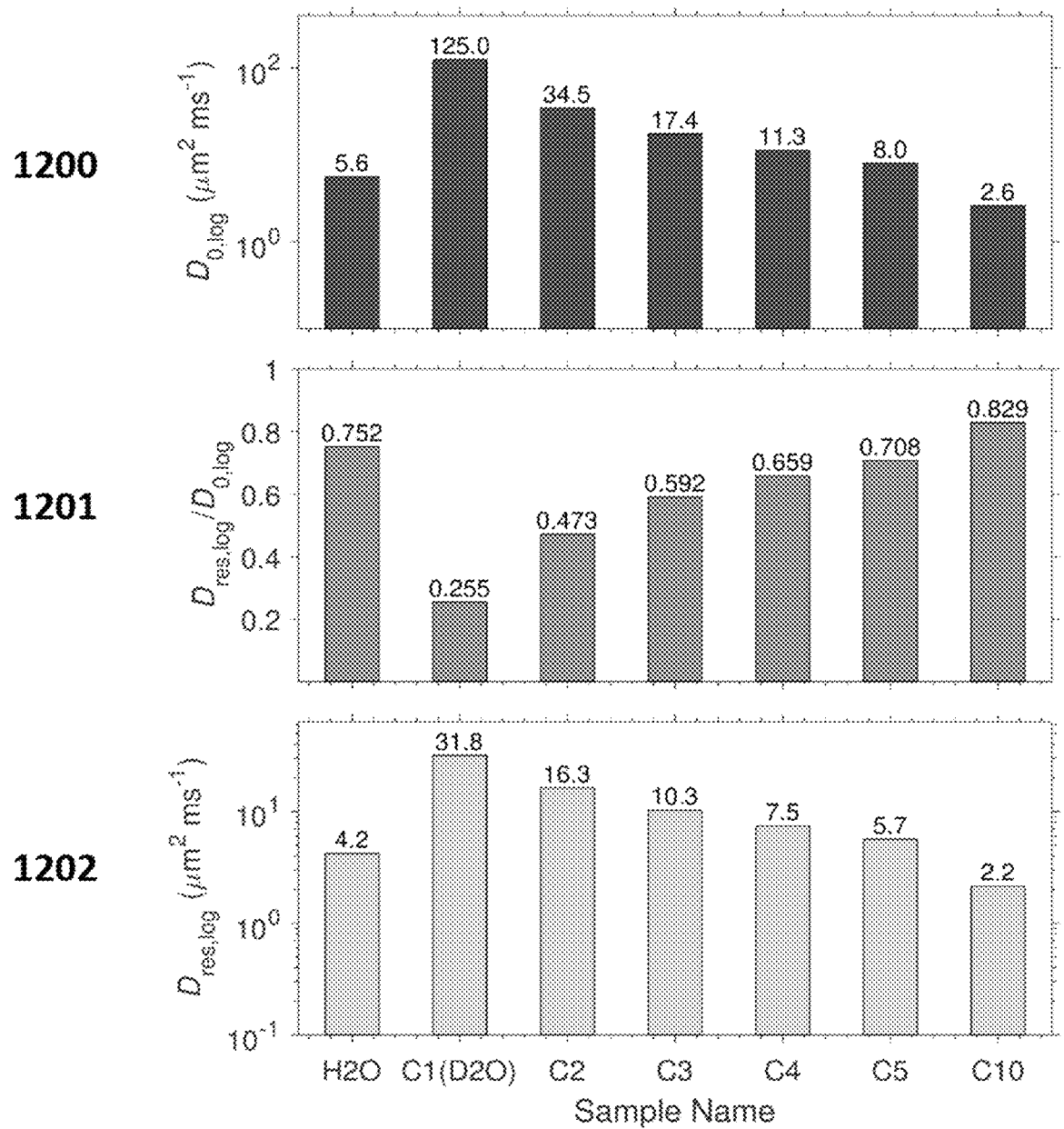
FIG. 19 show bar charts of diffusivities during $T_{2app}$ measurements under logging conditions.

FIG. 19 shows bar charts of diffusivities during $T_{2app}$ measurements under logging conditions. The top subplot 1200 is the estimated bulk diffusivity of fluids in the reservoir as listed in Table 2. The middle subplot 1201 is of the extrapolated normalized restricted diffusivity based on the diffusion length $L_D$ on logging conditions. The bottom subplot 1202 is the restricted diffusivity. For each subplot, the y-axis shows diffusivity. The x-axis indicates the fluid.

The middle subplot 1201 of FIG. 19 illustrates the normalized restricted diffusivity obtained by extrapolating the Padé fit to the diffusion length at logging conditions. These values confirm that the diffusion of all these fluids are restricted, to different extents. For example, methane is severely restricted with a normalized restricted diffusivity of only 26%. The calculated restricted diffusivities are presented in the bottom subplot of FIG. 19.

Figure 20:
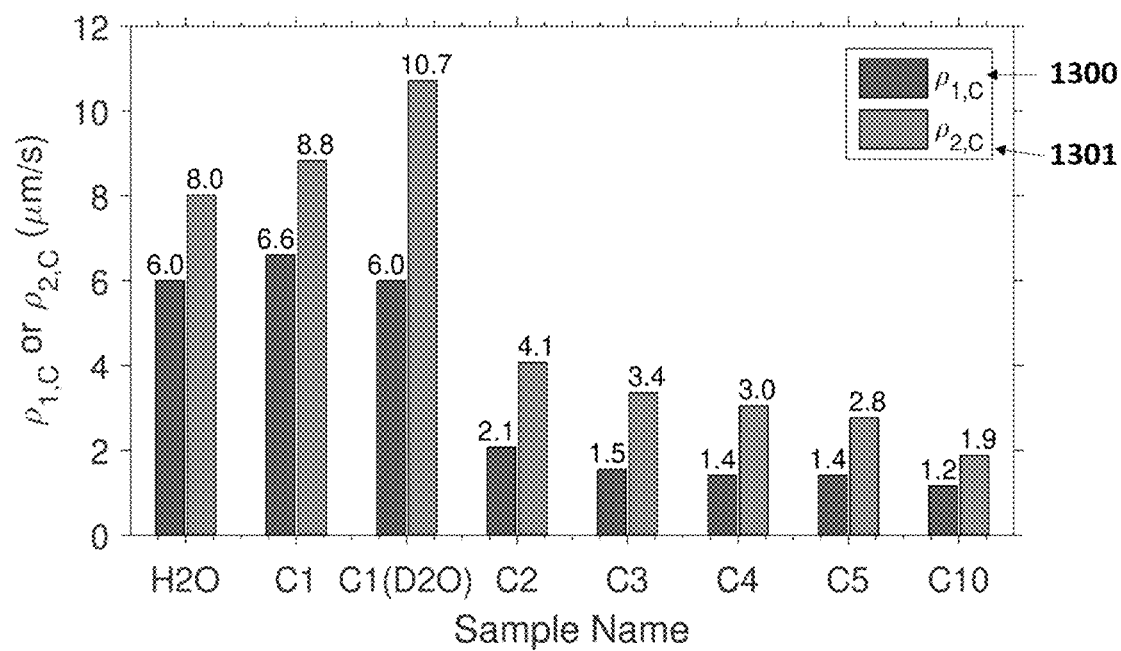
FIG. 20 is a comparison of surface relativities experienced by fluids in macro pores (region C).

The pore radius derived by the Padé fit can then be used to estimate the surface relaxivities, $\rho_1$ and $\rho_2$, of fluids in macropores (region C) under laboratory conditions by Equation 6:

$$\rho_1 = \frac{V}{ST_{1,s}} = \frac{r_p}{3T_{1,s}}, \quad (9)$$

$$\rho_2 = \frac{V}{ST_{2,s}} = \frac{r_p}{3T_{2,s}},$$

where $T_{1,s}$ and $T_{2,s}$ are the surface relaxation components of $T_1$ and $T_2$ respectively. They are approximated by $T_1$ and $T_2$ at the peak of region C where contributions from the bulk relaxation terms, $T_{1,b}$ and $T_{2,b}$, are negligible. The comparison of surface relaxivities of Land $T_2$, 1300 and 1301, respectively, experienced by fluids in macro pores (region C) is shown in FIG. 20.

Fluid Typing by $T_1/T_2$ AND $T_1/T_{2app}$

This section presents $T_1$-$T_2$ measurements conducted in the laboratory on as-received and saturated cores. The contrasts in $T_1/T_2$ and $T_1/T_{2app}$ are discussed in detail for fluid typing and saturation estimation.

Laboratory-Measured $T_1/T_2$

The laboratory-measured 2-D $T_1$-$T_2$ correlation map can be transformed into a $T_1/T_2$ vs. $T_2$ correlation map, as shown in FIGS. 21-24. For FIGS. 21-24, the top subplot (1400, 1500, 1600, 1700) is the projected $T_2$ distribution and the right subplot (1401, 1501, 1601, 1701) is the projected $T_1/T_2$ ratio distribution. The legends indicate the states of the cores, core number, saturating fluid, and NMR porosity assuming HI=1. The dashed horizontal line is the $T_1/T_2=1$ line.

FIGS. 21-24 show the $T_1/T_2$ vs. $T_2$ correlation maps of connate water and saturating fluids in the cores. It is found that the signal in region A (1410, 1510, 1610, 1710) has $T_1/T_2 \approx 10$ for both as-received and saturated states, indicating that the signal comes from viscous bitumen and/or hydrocarbons dissolved in kerogen (Singer et al., 2016; Chen et al., 2017; Singer et al., 2017; Singer et al., 2018). Furthermore, the signal intensity in region A increases after hydrocarbon saturation, but not after water saturation. This results from lowering the viscosity of the bitumen after mixing with the saturating hydrocarbons, which leads to longer $T_2$ and thereby more detectable signal (Yang et al., 2012; Singer et al., 2017; Singer et al., 2018), as well as more signal from the saturating hydrocarbons dissolved in the kerogen grains (Singer et al., 2016; Chen et al., 2017).

Figure 21:
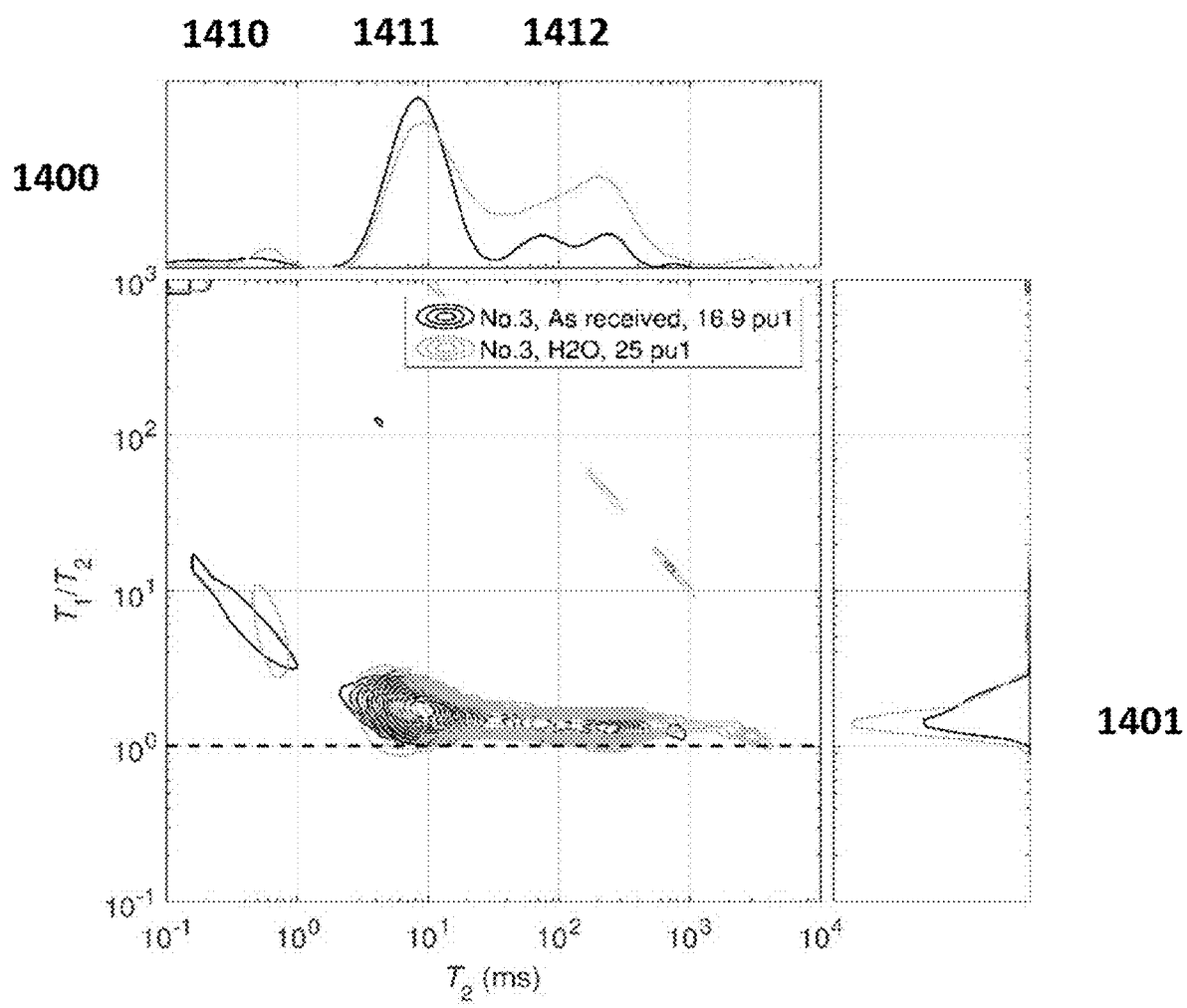
FIGS. 21-24 are 2-D correlation maps of as-received and fully-saturated cores, with $T_1/T_2$ ratio on the y-axis, $T_2$ on the x-axis and porosity perpendicular to the page.
Figure 22:
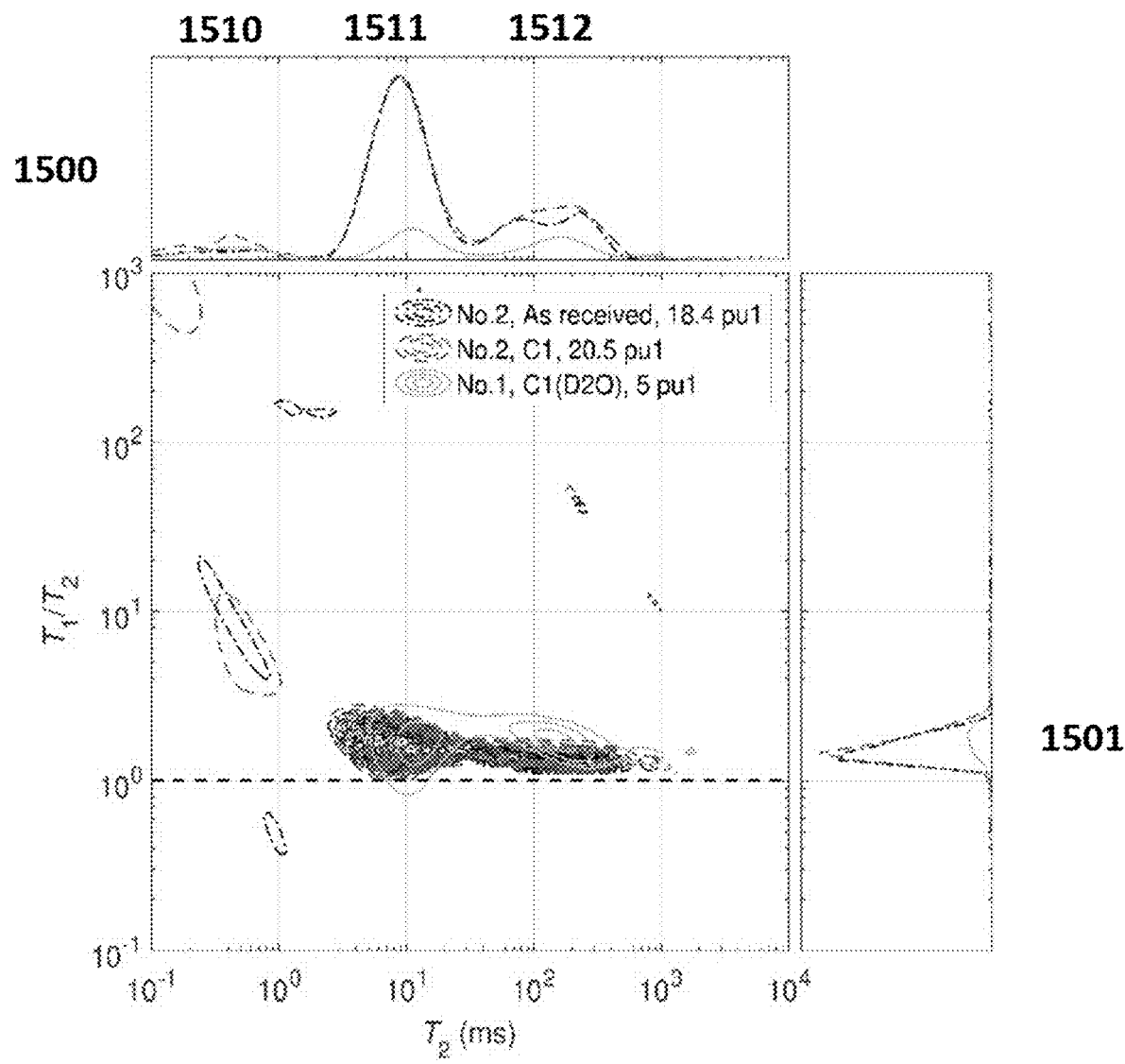
Figure 23:
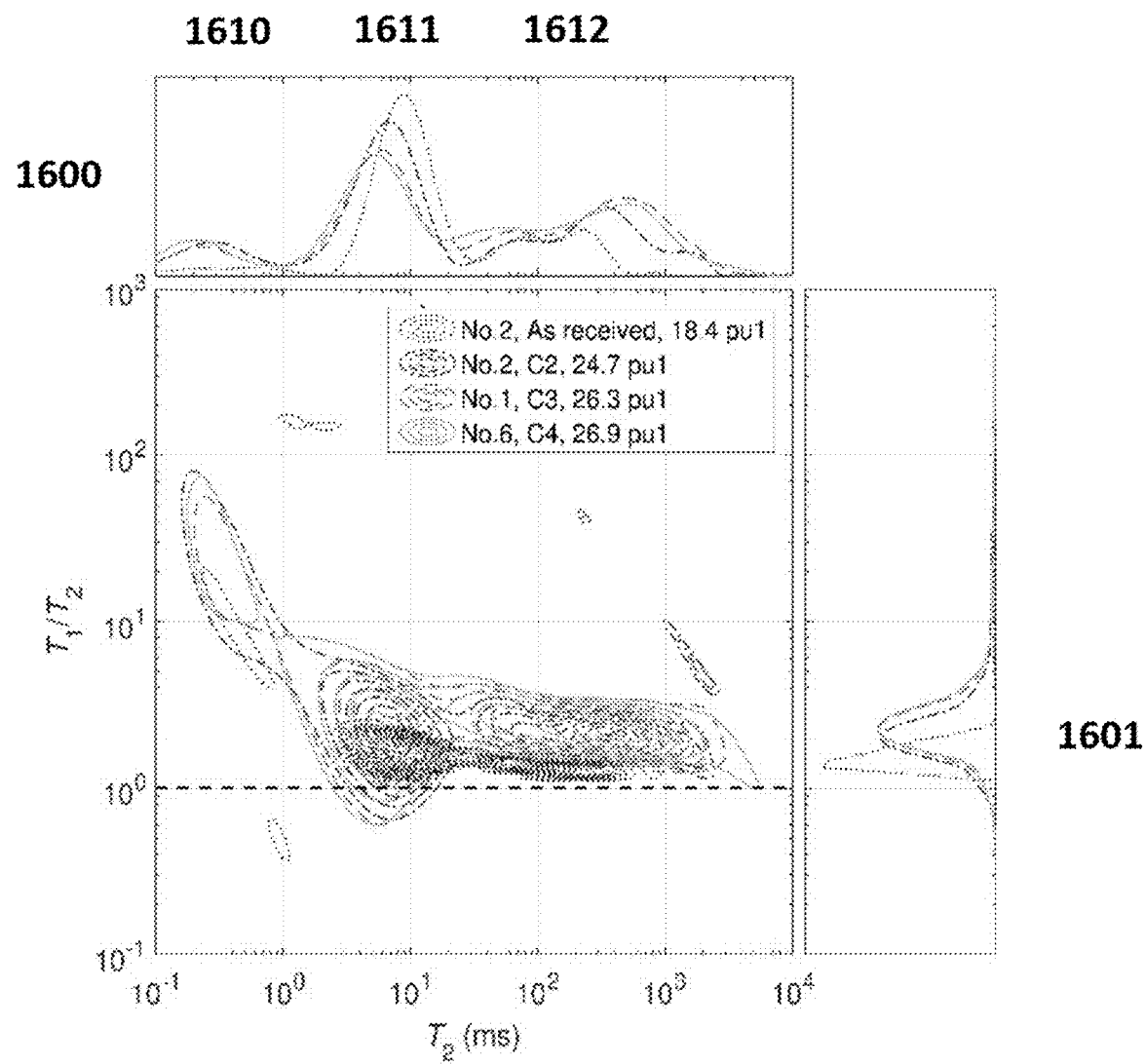
Figure 24:
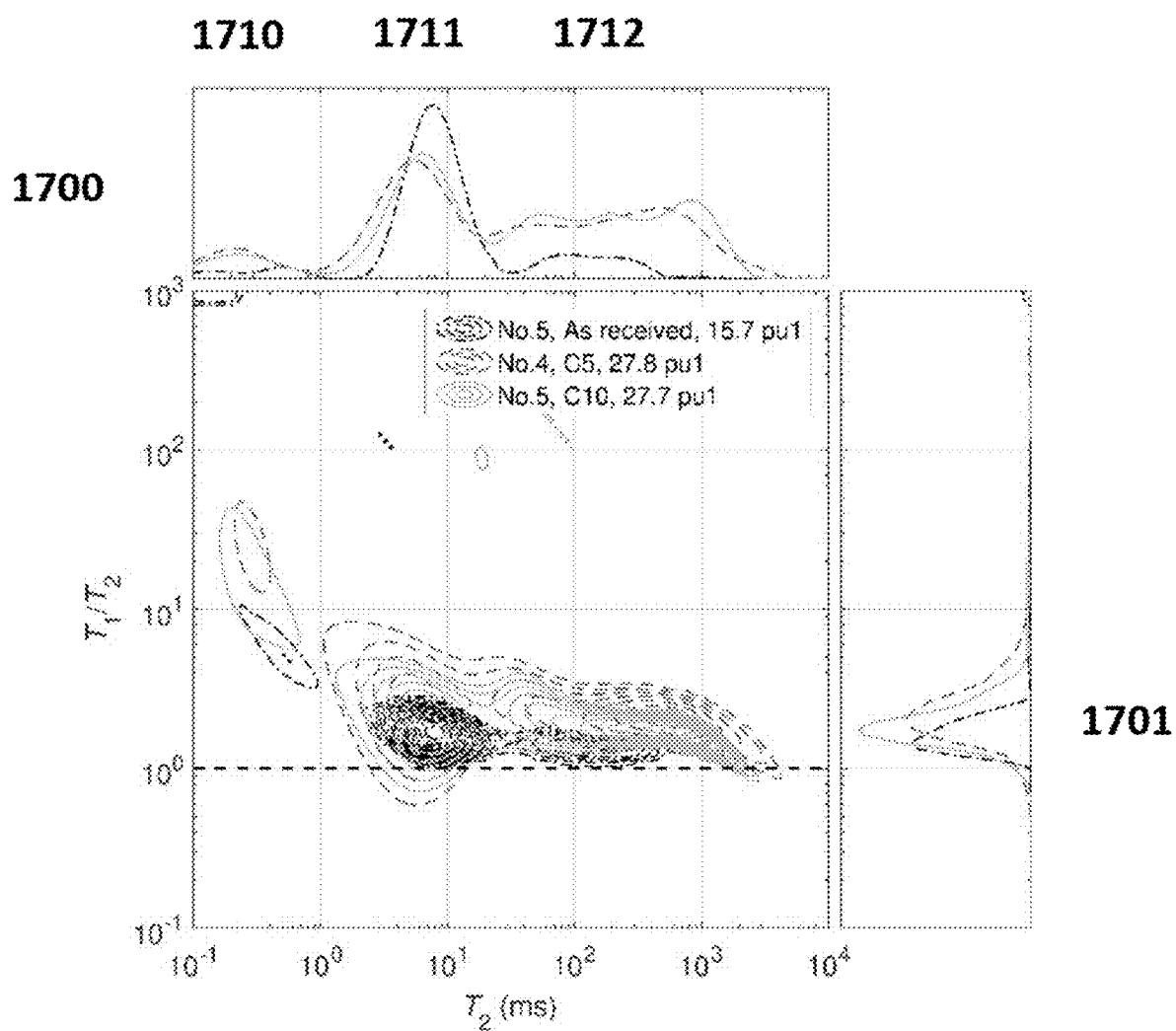

As for region B (1411) and C (1412), FIG. 21 indicates that saturating water has the same $T_1/T_2$ as connate water. The "C1" shown in FIG. 22 overlays with the "As-received" 2-D correlation map, which results from the low HI of methane. However, the pure methane signal shown in black suggests that methane in the core indeed has higher $T_1/T_2$ than connate water. As for the liquid hydrocarbons, FIGS. 23 and 24 also suggest that the saturating liquid-state hydrocarbons tend to yield broader $T_1/T_2$ distributions and higher $T_1/T_2$ ratios than connate water.

Figure 25:
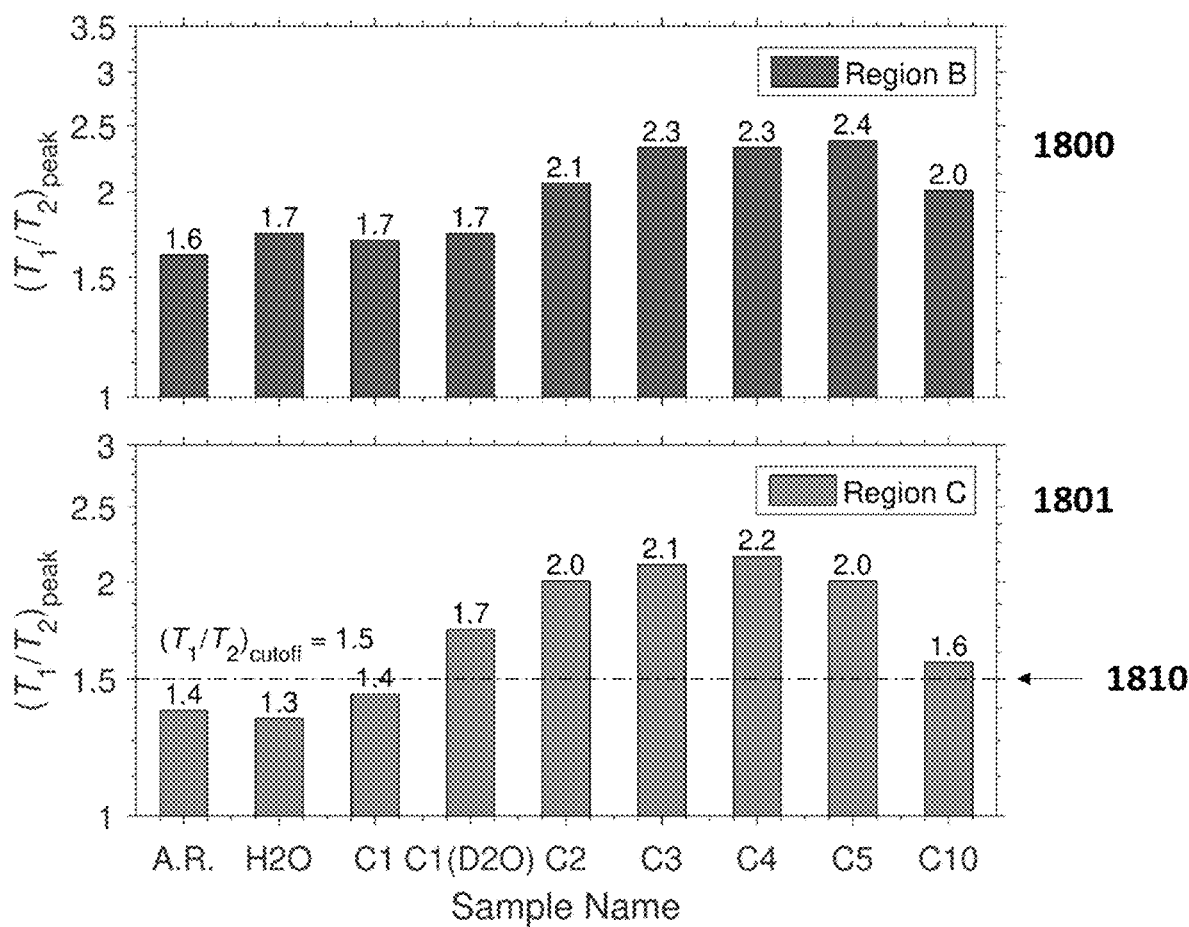
FIG. 25 is a comparison of $T_1/T_2$ ratio peak values in regions B and C.

The $T_1/T_2$ ratios at the peak of region B (1411, 1511, 1611, 1711) and C (1412, 1512, 1612, 1712) in FIGS. 21-24 is plotted in FIG. 25 in subplots 1800 and 1801, respectively. The reason for choosing the peak values instead of the commonly chosen log-mean values is that the peak values are subject to less interference from the connate water, especially in region C. The $T_1/T_2$ of region A is with large scattering expected in this short-$T_2$ region (i.e., lower resolution) such that the $T_1/T_2$ of region A is not plotted in FIG. 25.

The signal in region B is dominated by connate water, except for the case ("C1 (D2O)") where the core is deuterated beforehand. It is readily observed that the $T_1/T_2$ of light hydrocarbons in region C peaks at butane.

The light hydrocarbons in region C have higher $T_1/T_2$ than water. As a result, a $T_1/T_2$ cutoff~1.5 (indicated by the horizontal dashed line in the bottom subplot of FIG. 25, 1810) can be applied to distinguish water in macro pores from light hydrocarbons. This feature could be potentially exploited as a criterion for identifying water versus light hydrocarbons in core measurements.

Simulated Downhole-Measured $T_1/T_{2app}$

Figure 26:
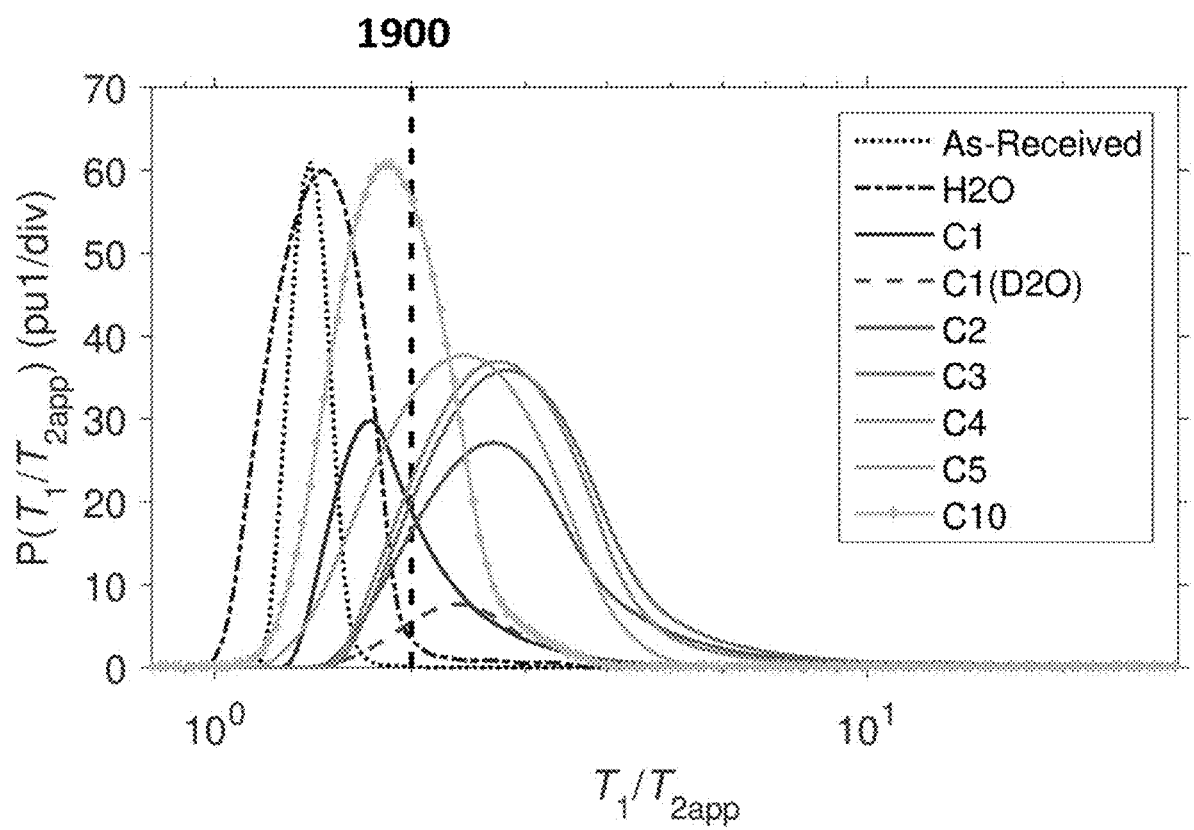
FIG. 26 is a plot of projected 1-D $T_1/T_{2app}$ distributions of the signals in region C from 2-D $T_1/T_{2app}$-$T_{2app}$ correlation maps.

The concept of calculating $T_{2app}$ by introducing the effect of magnetic-field gradient is then applied to 2-D $T_1$-$T_2$ correlation maps for $T_1$-$T_{2app}$ correlation maps (not shown). As a result, the $T_1/T_{2app}$ acquired by logging tools is reproduced from the laboratory measurements. The projected 1-D $T_1/T_{2app}$ distributions of the signal in region C are isolated and plotted in FIG. 26. The vertical dashed line 1900 is the proposed $T_1/T_{2app}=2$ cutoff separating lighter hydrocarbons from water and decane in region C. This plot also indicates that $T_1/T_{2app}$ distributions are broader for hydrocarbons compared to water.

Figure 27:
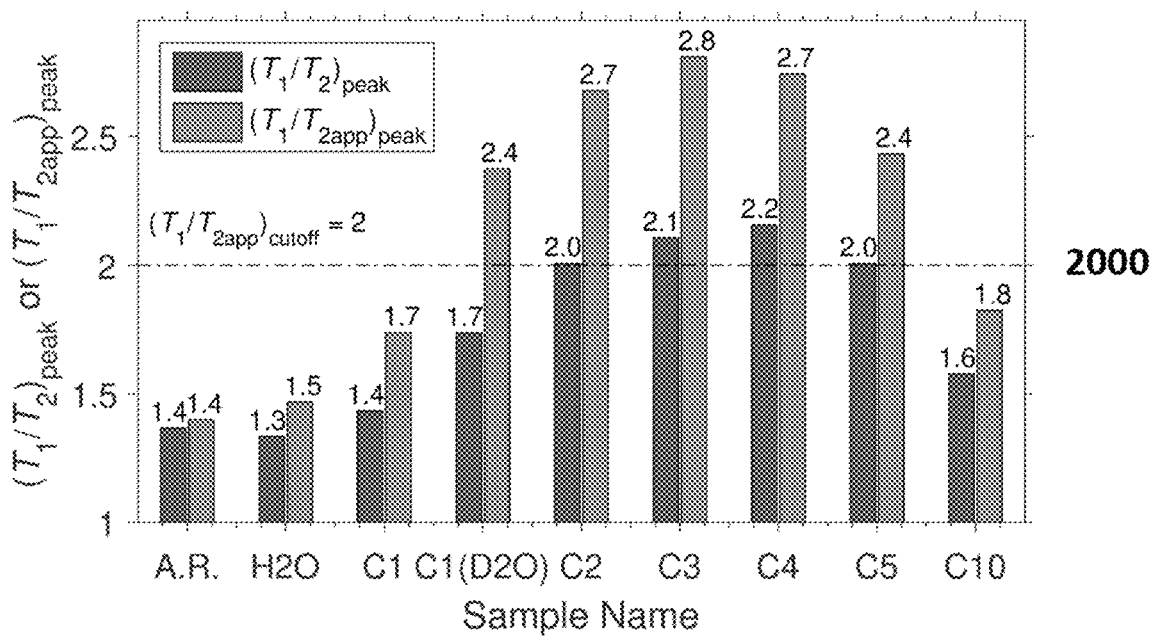
FIG. 27 shows $T_1/T_2$ and $T_1/T_{2app}$ at the peak of region C for the as-received state and different fluid saturations.

It should be noted that unlike the numerical mixing of $T_{2app}$, the connate-water signal is not compensated here because only the peak values of the $T_1/T_{2app}$ distributions in FIG. 27 are used as the representative $T_1/T_{2app}$ for saturating fluids. The peak value is used because it is less subjective to the interference of connate water. The comparison of $T_1/T_{2app}$ is presented in FIG. 27. It is obvious that the $T_1/T_{2app}$ amplifies the contrast compared to $T_1/T_2$. This finding suggests the downhole logs can more accurately separate fluids with different diffusivity using $T_1/T_{2app}$ contrast.

Thus, in an analogous way to which we obtained an optimal mix of $T_{2app}$ distributions of methane and the NGLs that best fit the $T_{2app}$ of the NMR log, it is also within the scope of this invention to obtain an optimal mix of $T_1/T_{2app}$ distributions of methane and NGLs that best fit the $T_1/T_{2app}$ distribution of the NMR log. This provides another measurement of the volumetric composition of methane and the NGLs in the reservoir.

It is readily observed that the methane and NGLs (i.e. ethane, propane, butane and pentane) yield higher values of $T_1/T_{2app}$ due to higher diffusivities compared to water and decane. Hence, a $T_1/T_{2app}$ cutoff about 2, denoted by the dashed lines in FIG. 27 (2000) and FIG. 28 (2100), can be applied to distinguish methane and NGLs from other fluids, such as water and heavier hydrocarbons like decane, in the downhole NMR logs. A $T_1/T_{2app}$ cutoff about 1.7 (2101) can be used to separate water in both micro and macro pores from hydrocarbons.

Figure 28:
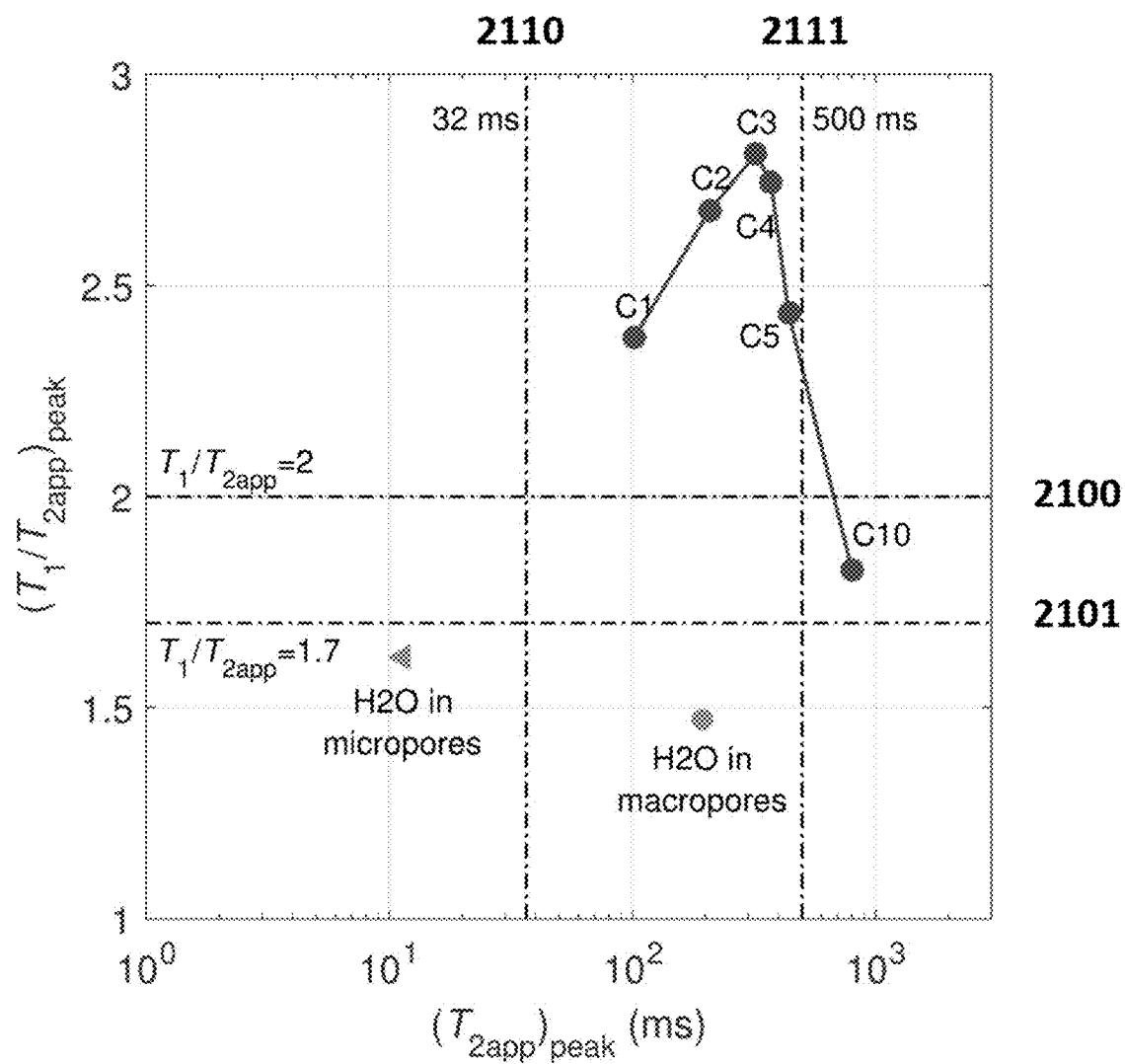
FIG. 28 shows $T_1/T_{2app}$ vs. $T_{2app}$ of connate water and saturating fluids.

In addition to $T_1/T_{2app}$ cutoff, $T_{2app}$ can provide additional information for fluid typing. The peak values on the $T_1/T_{2app}$ vs. $T_{2app}$ correlation maps (not shown) are plotted in FIG. 28. FIG. 28 shows that NGLs have $T_{2app}$ shorter than 500 ms (2111). Therefore, one can apply a $T_{2app}$ cutoff at 500 ms in addition to the $T_1/T_{2app}$ cutoff to separate NGLs from water and decane. This can lead to a more robust result for fluid typing. By applying $T_1/T_{2app}$ cutoffs (1.7 and 2) and $T_{2app}$ cutoff (500 ms), one can also separate heavier alkanes, such as decane, from the light hydrocarbons.

REFERENCES CITED

Chen, Z.; Singer, P. M.; Jun, K.; Vargas, F. P.; Hirasaki, G. J.; Jun, K.; Vargas, F. P.; Hirasaki, G. J. Effects of Bitumen Extraction on the 2D NMR Response of Saturated Kerogen Isolates. *Petrophysics* 2017, 58, 470-484.

Fleury, M.; Romero-Sarmiento, M. Characterization of Shales Using $T_1$-$T_2$ NMR Maps. *Journal of Petroleum Science and Engineering* 2016, 137, 55-62.

Hürlimann, M. D.; Helmer, K. G.; Latour, L. L.; Sotak, C. H. Restricted Diffusion in Sedimentary Rocks. Determination of Surface-Area-to-Volume Ratio and Surface Relaxivity. *Journal of Magnetic Resonance, Series A* 1994, 111, 169-178.

Hürlimann, M. D.; Freed, D. E.; Zielinski, L. J.; Song, Y. Q.; Leu, G.; Straley, C.; Minh, C. C.; Boyd, A. Hydrocarbon Composition from NMR Diffusion and Relaxation Data. *Petrophysics* 2009, 50, 116-129.

Kausik, R.; Minh, C. C.; Zielinski, L.; Vissapragada, B.; Akkurt, R.; Song, Y.; Liu, C.; Jones, S.; Blair, E. Characterization of Gas Dynamics in Kerogen Nanopores by NMR. *SPE* 147198, 2011, 1-16.

Kausik, R.; Fellah, K.; Rylander, E.; Singer, P. M.; Lewis, R. E.; Sinclair, S. M. NMR Relaxometry in Shale and Implications for Logging. *Petrophysics* 2016, 57, 339-350.

Krynicki, K.; Green, C. D.; Sawyer, D. W. Pressure and Temperature Dependence of Self-Diffusion in Water. *Faraday Discussions of the Chemical Society* 1978, 66, 199-208.

Latour, L. L.; Mitra, P. P.; Kleinberg, R. L.; Sotak, C. H. Time-Dependent Diffusion Coefficient of Fluids in Porous Media as a Probe of Surface-to-Volume Ratio. *Journal of Magnetic Resonance, Series A* 1993, 101, 342-346.

Lo, S.-W.; Hirasaki, G. J.; House, W. V.; Kobayashi, R. Mixing Rules and Correlations of NMR Relaxation Time with Viscosity, Diffusivity, and Gas/Oil Ratio of Methane/Hydrocarbon Mixtures. *Society of Petroleum Engineers (SPE) Journal* 2002, 7, 1-4.

Minh, C. C.; Crary, S.; Singer, P. M.; Valori, A.; Bachman, N.; Hursan, G. G.; Ma, S. M.; Belowi, A.; Kraishan, G. Determination of Wettability from Magnetic Resonance Relaxation and Diffusion Measurements on Fresh-State Cores. *SPWLA 56th Annual Logging Symposium* 2015.

Mitchell, J.; Gladden, L. F.; Chandrasekera, T. C.; Fordham, E. J. Low-Field Permanent Magnets for Industrial Process and Quality Control. *Progress in Nuclear Magnetic Resonance Spectroscopy* 2014, 76, 1-60.

Oosting, P. H.; Trappeniers, N. J. Proton Spin-Lattice Relaxation and Self-Diffusion in Methanes. I. Spin-Echo Spectrometer and Preparation of the Methane Samples. *Physica* 1971, 51, 395-417.

Singer, P. M.; Chen, Z.; Hirasaki, G. J. Fluid Typing and Pore Size in Organic Shale using 2D NMR in Saturated Kerogen. *Petrophysics* 2016, 57, 604-619.

Singer, P. M.; Chen, Z.; Alemany, L. B.; Hirasaki, G. J.; Zhu, K.; Xie, Z. H. Z. H.; Vo, T. D. NMR Relaxation of Polymer-Alkane Mixes, A Model System for Crude Oils. *SPWLA 58th Annual Logging Symposium* 2017.

Singer, P. M.; Asthagiri, D.; Chapman, W. G.; Hirasaki, G. J. Molecular Dynamics Simulations of NMR Relaxation and Diffusion of Bulk Hydrocarbons and Water. *Journal of Magnetic Resonance* 2017, 277, 15-24.

Singer, P. M.; Chen, Z.; Alemany, L. B.; Hirasaki, G. J.; Zhu, K.; Xie, Z. H.; Vo, T. D. Interpretation of NMR Relaxation in Bitumen and Organic Shale Using Polymer-Heptane Mixes. *Energy & Fuels* 2018, 32, 1534-1549.

Singer, P. M.; Asthagiri, D.; Chapman, W. G.; Hirasaki, G. J. NMR Spin-Rotation Relaxation and Diffusion of Methane. *The Journal of Chemical Physics* 2018, 148.

Singer, P. M.; Asthagiri, D.; Chen, Z.; Valiya Parambathu, A.; Hirasaki, G. J.; Chapman, W. G. Role of Internal Motions and Molecular Geometry on the NMR Relaxation of Hydrocarbons. *Journal of Chemical Physics* 2018, 148.

Sigal, R. F. Pore-Size Distributions for Organic-Shale-Reservoir Rocks from Nuclear-Magnetic-Resonance Spectra Combined with Adsorption Measurements. *Society of Petroleum Engineers (SPE) Journal* 2015, 20, 1-7.

Thern, H.; Horch, C.; Stallmach, F.; Li, B.; Mezzatesta, A.; Zhang, H.; Arro, R. Low-field NMR Laboratory Measurements of Hydrocarbons Confined in Organic Nanoporous Media at Various Pressures. *Microporous and Mesoporous Materials* 2018, 269, 21-25.

Tinni, A.; Sondergeld, C.; Rai, C. New Perspectives on the Effects of Gas Adsorption on Storage and Production of Natural Gas from Shale Formations. 2018, 59, 99-104.

Valori, A.; Van Den Berg, S.; Ali, F.; Abdallah, W. Permeability Estimation from NMR Time Dependent Methane Saturation Monitoring in Shales. *Energy & Fuels* 2017, 31, 5913-5925.

Venkataramanan, L.; Song, Y.; Hürlimann, M. D. Solving Fredholm Integrals of the First Kind with Tensor Product Structure in 2 and 2.5 Dimensions. *IEEE Transaction on Signal Processing* 2002, 50 (5), 1017-1026.

Wang, H. J.; Mutina, A.; Kausik, R. High-field Nuclear Magnetic Resonance Observation of Gas Shale Fracturing by Methane Gas. *Energy & Fuels* 2014, 28, 3638-3644.

Yang, Z.; Hirasaki, G. J.; Appel, M.; Reed, D. A. Viscosity Evaluation for NMR Well Logging of Live Heavy Oils. *Petrophysics* 2012, 53, 22-37.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons skilled in the art.

The invention claimed is:

1. A method of measuring at least one of:
(i) respective downhole concentrations in a subsurface formation of one or more members of the C1-C5 alkane group consisting of methane, ethane, propane, butane and pentane;
(ii) a ratio between respective downhole concentrations of multiple members of the C1-C5 alkane group, and
(iii) a linear combination of ratios between respective downhole concentrations of multiple members of the C1-C5 alkane group:
the method comprising:
a. obtaining sample(s) of core from a target depth in a subsurface formation;
b. obtaining downhole NMR log data of the subsurface formation at the target depth;

c. when a given one of the core sample(s) is saturated with a first pressurized saturation fluid comprising a first member of the C1-C5 alkane group, obtaining first laboratory NMR data of the saturated core-sample(s); and d. when the same given one or a different one of the core sample(s) is saturated with a second pressurized saturation fluid that is different from the first pressurized saturation fluid, the second saturation fluid comprising a second member of the C1-C5 alkane group that is different from the first member, obtaining second laboratory NMR data of the saturated core-sample(s), wherein the first and second laboratory NMR data collectively form a laboratory NMR data set, and wherein the method further comprises:

e. computing from the lab-NMR data set and the downhole NMR log data at least one downhole parameter selected from the group consisting of:

(i) respective downhole concentrations of one or more members of the C1-C5 alkane group consisting of methane, ethane, propane, butane and pentane; and (ii) a ratio between respective downhole concentrations of multiple members of the C1-C5 alkane group.

2. The method of claim 1 wherein:

i. the method further comprises: when the same given one or a different one of the core sample(s) is saturated with a third pressurized saturation fluid comprising a third member of the C1-C5 alkane group that is different from the first and second members, obtaining third laboratory NMR data of the saturated core-sample(s); and ii. the third pressurized saturation fluid is different from both of the first and second pressurized saturation fluids; and iii. the first, second and third laboratory NMR data collectively form the laboratory NMR data set.

3. The method of claim 2 wherein:

i. the method further comprises: when the same given one or a different one of the core sample(s) is saturated with a fourth pressurized saturation fluid comprising a fourth member of the C1-C5 alkane group that is different from the first, second and third members, obtaining fourth laboratory NMR data of the saturated core-sample(s); and ii. the 4th pressurized saturation fluid is different from all of the first, second, and 3rd pressurized saturation fluids; and iii. the first, second, third and fourth laboratory NMR data collectively form the laboratory NMR data set.

4. The method of claim 3 wherein:

i. the method further comprises: when the same given one or a different one of the core sample(s) is saturated with a fifth pressurized saturation fluid comprising a fifth member of the C1-C5 alkane group that is different from the first, second, third and fourth members, obtaining fifth laboratory NMR data of the saturated core-sample(s); and ii. the fifth pressurized saturation fluid is different from all of the first, second, 3rd and 4th pressurized saturation fluids; and iii. the first, second, third, fourth and fifth laboratory NMR data collectively form the laboratory NMR data set.

5. The method of claim 1 wherein the downhole pressure and/or temperature are estimated for the subsurface formation at the target depth, and wherein the $1^{st}$ and/or $2^{nd}$ and/or $3^{rd}$ and/or $4^{th}$ and/or $5^{th}$ laboratory NMR data is obtained when the core sample(s) are saturated with the first and/or second and/or third and/or fourth and/or fifth pressurized saturation fluid at the estimated pressure and temperature.

6. The method of claim 1 wherein the laboratory NMR data and/or downhole NMR log data comprises one or more of (i.e. any combination of): T2 distribution data, T2apparent distribution data, T1 distribution data, T1/T2 data, T1/T2apparent, D (diffusion) vs. T2 data, D (diffusion) vs T2apparent data.

7. The method of claim 1 wherein the computing of the at least one downhole parameter comprises optimizing a fit of:

i. a mathematical combination of the 1St and/or $2^{nd}$ and/or $3^{rd}$ and/or 4th and/or 5th laboratory NMR data; to ii. downhole NMR data.

8. The method of claim 7 wherein the computed downhole concentration and/or computed molar fraction of the $1^{st}$ and/or $2^{nd}$ and/or $3^{rd}$ and/or $4^{th}$ and/or $5^{th}$ member of the C1-C5 alkane group corresponds to a weighting coefficient for the $1^{st}$ and/or $2^{nd}$ and/or $3^{rd}$ and/or $4^{th}$ and/or $5^{th}$ laboratory NMR data.

9. The method of claim 1 performed to compute at least one of the following:

(i) a ratio between a downhole methane concentration and a downhole ethane concentration;

(ii) a ratio between a downhole methane concentration and a downhole propane concentration;

(iii) a ratio between a downhole methane concentration and a downhole butane concentration;

(iv) a ratio between a downhole methane concentration and a downhole pentane concentration; and/or (v) any ratio involving any of C1-C5 alkane group.

10. The method claim 1, performed to compute at least one of the following:

(i) a multi-alkane sum of downhole concentrations of ethane and/or propane and/or butane and/or pentane; and (ii) a ratio between the multi-alkane sum and a downhole methane concentration.

11. The method of claim 1 performed for a plurality of target depths to characterize the subsurface reservoir at multiple target depths.

12. The method of claim 1 wherein the computing comprises converting T2 data into T2apparent data or vice versa using at least one of:

(i) an estimated restricted diffusion coefficient for one or more members of the C1-C5 alkane group; and/or (ii) an estimated mean pore-size of the core sample(s).

13. The method of claim 12 wherein the restricted diffusion coefficient is computed by interpolating the following method:

a method using NMR to determine the mean pore-size and tortuosity of the light hydrocarbon-filled porosity in a reservoir formation by:

a) Obtaining core in selected zones from the reservoir formation, b) Measuring NMR on the core in the laboratory including normalized diffusion coefficient D/Do as a function of diffusion time using one or more hydrogen-bearing fluids selected from the list (H2, HD, CH4, C2H6, C3H8, C4H10, C5H12) saturating the core, c) Varying the pressure and/or temperature of the one or more hydrogen-bearing fluids to vary the diffusion length in the NMR measurement, and d) Computing the mean pore-size and tortuosity of the light hydrocarbon-filled porosity of the reservoir formation from D/Do versus diffusion length of the hydrogen-bearing fluid using a numerical model for restricted diffusion in a porous medium.

14. The method of claim 1 wherein the NMR log is from a gradient-based NMR tool.

15. The method of claim 1 wherein
   (i) a molar fraction of the first member of the C1-C5 alkane group within the first saturation fluids is at least 0.9, and
   (ii) a molar fraction of the second member of the C1-C5 alkane group within the second saturation fluids is at least 0.9.

16. The method of claim 2 wherein
   (i) a molar fraction of the first member of the C1-C5 alkane group within the first saturation fluids is at least 0.9,
   (ii) a molar fraction of the second member of the C1-C5 alkane group within the second saturation fluids is at least 0.9; and
   (iii) a molar fraction of the third member of the C1-C5 alkane group within the third saturation fluids is at least 0.9.

17. The method of claim 3 wherein
   (i) a molar fraction of the first member of the C1-C5 alkane group within the first saturation fluids is at least 0.9,
   (ii) a molar fraction of the second member of the C1-C5 alkane group within the second saturation fluids is at least 0.9;
   (iii) a molar fraction of the third member of the C1-C5 alkane group within the third saturation fluids is at least 0.9; and
   (iv) a molar fraction of the fourth member of the C1-C5 alkane group within the fourth saturation fluids is at least 0.9.

18. The method of claim 4 wherein
   (i) a molar fraction of the first member of the C1-C5 alkane group within the first saturation fluids is at least 0.9,
   (ii) a molar fraction of the second member of the C1-C5 alkane group within the second saturation fluids is at least 0.9;
   (iii) a molar fraction of the third member of the C1-C5 alkane group within the third saturation fluids is at least 0.9;
   (iv) a molar fraction of the fourth member of the C1-C5 alkane group within the fourth saturation fluids is at least 0.9; and
   (v) a molar fraction of the fifth member of the C1-C5 alkane group within the fifth saturation fluids is at least 0.9.

19. A method of measuring at least one of:
   (i) respective downhole concentrations in a subsurface formation of one or more members of the C1-C5 alkane group consisting of methane, ethane, propane, butane and pentane; and
   (ii) a ratio between respective downhole concentrations of multiple members of the C1-C5 alkane group, the method comprising:
   a. obtaining sample(s) of core from a target depth in a subsurface formation;
   b. obtaining downhole NMR log data of the subsurface formation at the target depth;
   c. when a given one of the core sample(s) is saturated with a first pressurized saturation fluid comprising a first member of the C1-C5 alkane group, obtaining first laboratory NMR data of the saturated core-sample(s); and
   d. when the same given one or a different one of the core sample(s) is saturated with a second pressurized saturation fluid that is different from the first pressurized saturation fluid, the second saturation fluid comprising a second member of the C1-C5 alkane group that is different from the first member, obtaining second laboratory NMR data of the saturated core-sample(s), wherein the first and second laboratory NMR data collectively form a laboratory NMR data set, and wherein the method further comprises:
   e. computing from the lab-NMR data set and the downhole NMR log data at least one downhole parameter selected from the group consisting of:
   (i) respective downhole concentrations of one or more members of the C1-C5 alkane group consisting of methane, ethane, propane, butane and pentane; and
   (ii) a ratio between respective downhole concentrations of multiple members of the C1-C5 alkane group.

20. A method of measuring at least one of:
   (i) respective downhole concentrations in a subsurface formation of one or more members of the C1-C5 alkane group consisting of methane, ethane, propane, butane and pentane; and
   (ii) a mathematical function of respective downhole concentrations of multiple members of the C1-C5 alkane group, the method comprising:
   a. obtaining sample(s) of core from a target depth in a subsurface formation;
   b. obtaining downhole NMR log data of the subsurface formation at the target depth;
   c. when a given one of the core sample(s) is saturated with a first pressurized saturation fluid comprising a first member of the C1-C5 alkane group, obtaining first laboratory NMR data of the saturated core-sample(s); and
   d. when the same given one or a different one of the core sample(s) is saturated with a second pressurized saturation fluid that is different from the first pressurized saturation fluid, the second saturation fluid comprising a second member of the C1-C5 alkane group that is different from the first member, obtaining second laboratory NMR data of the saturated core-sample(s), wherein the first and second laboratory NMR data collectively form a laboratory NMR data set, and wherein the method further comprises:
   e. computing from the lab-NMR data set and the downhole NMR log data at least one downhole parameter selected from the group consisting of:
   (i) respective downhole concentrations of one or more members of the C1-C5 alkane group consisting of methane, ethane, propane, butane and pentane; and
   (ii) a mathematical function between respective downhole concentrations of multiple members of the C1-C5 alkane group.

* * * * *